(12) United States Patent
El-Salhy

(10) Patent No.: US 6,518,246 B1
(45) Date of Patent: Feb. 11, 2003

(54) PHARMACEUTICAL COMPOSITION AND METHOD FOR THE TREATMENT OF NEOPLASTIC CELLS

(76) Inventor: Magdy El-Salhy, Norra Slevgränd 149, S-906 27 Umeå (SE)

( * ) Notice: Subject to any disclaimer, the term of this patent is extended or adjusted under 35 U.S.C. 154(b) by 0 days.

(21) Appl. No.: 09/994,841

(22) Filed: Nov. 28, 2001

(51) Int. Cl.$^7$ ...................... A61K 38/00; A61K 31/445; A61K 51/00; A61K 38/31
(52) U.S. Cl. ............................... 514/16; 514/2; 514/12; 514/330; 530/300; 530/311; 530/324; 530/329; 424/1.45; 424/184.1; 424/198.1
(58) Field of Search ............................... 514/2, 12, 16, 514/330; 530/300, 311, 324, 329; 424/1.45, 184.1, 198.1

(56) References Cited

PUBLICATIONS

Iishi, et al., Int. J. Cancer:61, 861–863(1995) (see, e.q., the abstract) (see also Materials and Methods).*
Lubbe et al., Int. J. Microvirc. 1994; 14:218–225 (see at least the abstract).*
Goldberg et al., Cancer, Sep. 15, 1995; 76(6):961–966.*
R. Midgley et al., "Colorectal Cancer," *The Lancet*, V. 353, 1999, pp. 391–399.
T. Berge et al., "Carcinoma of the Colon and Rectum in a Defined Population," *Acta Chirurgica Scandinavica*, Supplementum 438, 1973, pp. 9–11, 13–21, 24–43, 45–69, 71–76, 78–86.
Frank H. Valone et al., "A Northern California Oncology Group Randomized Trial of Leucovorin Plus 5–Fluorouracil Versus Sequential Methotrexate, 5–Fluorouracil, and Leucovorin in Patients with Advanced Colorectal Cancer Who Failed Treatment with 5–Fluorouracil or 5–Fluorodeoxyuridine Alone," *NCI Monographs*, No. 5, 1987, pp. 175–177.
Mohammed Mohiuddin et al., "Adjuvant Radiation Therapy for Colon and Rectal Cancer," *Seminars in Oncology*, V. 18, 1991, pp. 411–420.
M. Sue O'Dorisio, "Neuropeptides and Gastrointestinal Immunity," *The American Journal of Medicine*, V. 81 ( Suppl. 6B), pp. 74–82.
Magdy El–Salhy et al., "Low Levels of Colonic Somatostatin and Galanin in Patients with Colon Carcinoma," *GI Cancer*, V. 2(3), pp. 221–225.
Magdy El–Salhy et al., "Colonic Endocrine Cells in Rectal Carcinoma, with Particular Regard to Preoperative Irradiation," *GI Cancer*, V. 2(4), pp. 285–292.
Magdy El–Salhy et al., "Colonic Endocrine Cells in Patients with Carcinoma of the Colon," *European Journal of Gastroenterology & Hepatology*, V. 10, 1998, pp. 517–522.
Edwin E. Daniel (editor), *Neuropeptide Function in the Gastrointestinal Tract*, CRC Press, Inc., pp. 479–490.

* cited by examiner

*Primary Examiner*—Christopher S. F. Low
*Assistant Examiner*—B. Dell Chism
(74) *Attorney, Agent, or Firm*—Young and Thompson

(57) ABSTRACT

A pharmaceutical composition and method, for treating human or non-human neoplastic disorders, e.g. colorectal disorders, comprising the administration of pharmaceutically effective amounts of galanin, octreotide and serotonin in a pharmaceutically acceptable carrier. The effective amount is 10 µg/kg body weight to about 60 µg/kg body weight of each of the three, preferably about 10 µg/kg to about 20 µg/kg of each of the three.

6 Claims, 12 Drawing Sheets

PHARMACEUTICAL COMPOSITION AND METHOD FOR THE TREATMENT OF NEOPLASTIC CELLS

NEW COMPOSITION AND USE

Figure 1:
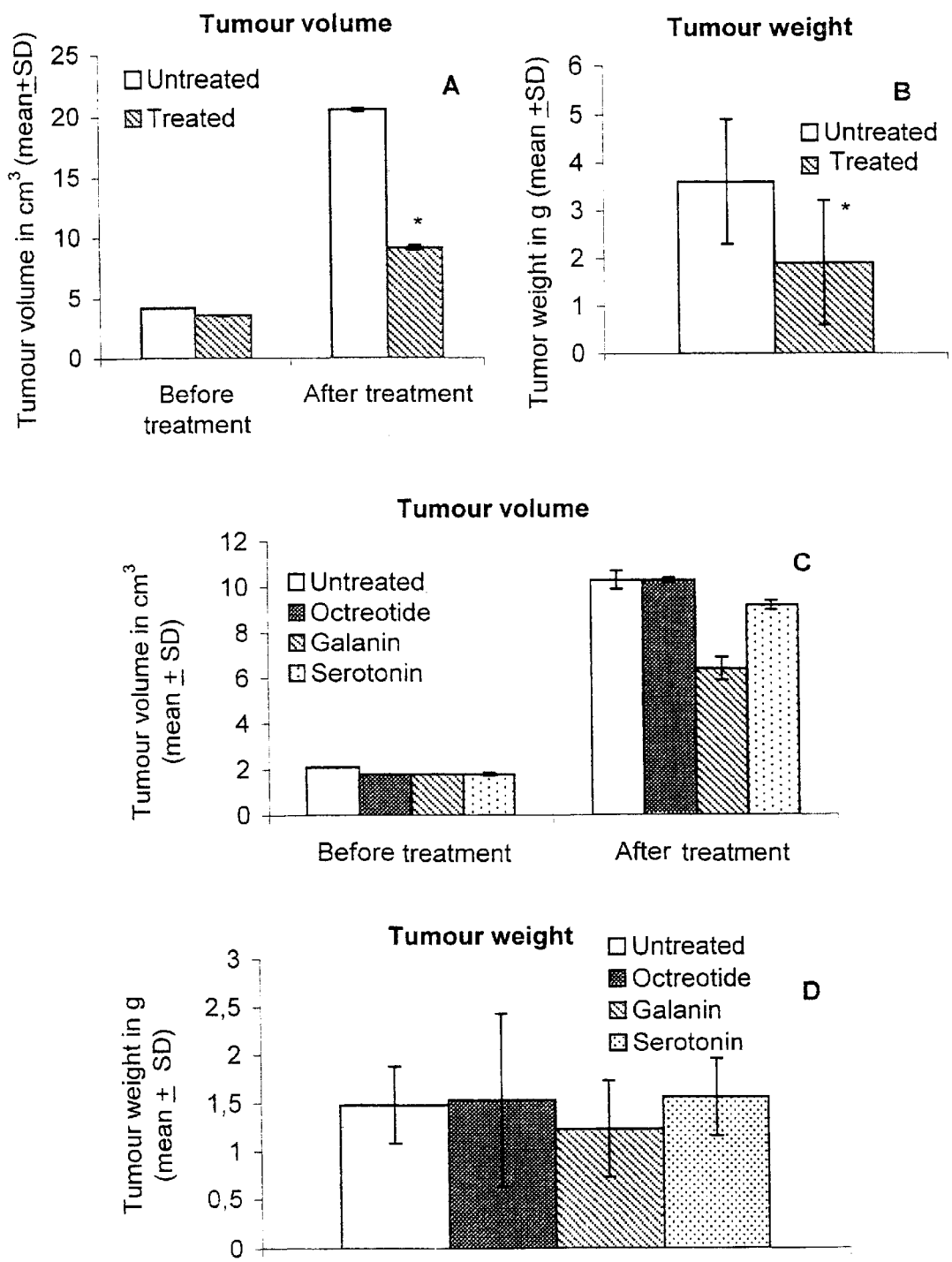

The present invention relates to a pharmaceutical composition comprising pharmaceutically active amounts of galanin, octreotide and serotonin, respectively, and a pharmaceutically acceptable carrier. Also said composition comprising galanin, octreotide and serotonin, for medical use is disclosed. A method for treating a human or non-human animal with a disorder, or may potentially be affected by a disorder, associated with neoplastic cells, comprising the step of administering an above composition is also disclosed.

BACKGROUND TO THE INVENTION

Colorectal cancer is a major cause of morbidity and mortality in non-smokers in the western world, with 300,000 new cases diagnosed in Europe and in the USA each year (Midgely and Kerr, 1999). Around 50% of these patients develop metastatic disease after surgical resection of the primary tumour, or it may be initially present with advanced disease (Berger et al, 1973). Colorectal carcinoma is relatively resistant to chemotherapy, and radiation therapy is usually used only for palliative purposes (Valone et al., 1987; Muhiuddin and Karks, 1991).

The neuroendocrine peptides and amines of the gut play a significant role in regulating the proliferation and growth of gastrointestinal epithelial and mesenchymal cells (Hill, 1991). These bioactive substances are also involved in regulating the local immune defence of the gut (O'Dorisio, 1987). Both cell proliferation and local immune defence of the gut are important in the development and growth of colorectal cancer. It was speculated that there might be an abnormality in the neuroendocrine system in the colon of patients with colon carcinoma that might initiate and/or promote the development of the colorectal carcinoma (E1-Salhy et al., 1998a). In support of this assumption is the finding of low levels of somatostatin and galanin, and decreased cell density of somatostatin and serotonin in the colon of patients with colon carcinoma (E1-Salhy et al, 1998a; 1988b). Furthermore, the number of colonic somatostatin and serotouni cells was restored in patients with rectal carcinoma that received pre-operative radiotherapy (E1-Salhy et al., 1988c). As pre-operative radiotherapy has been found to improve 5- and 10-year survival rates and to reduce local recurrences, it would seem that restoring the number of these endocrine cells in these patients plays a role in improving their prognosis.

There is however still a need for new compositions and methods for therapy for treating disorders associated with neoplastic cells, e.g. colorectal cancer.

SUMMARY OF THE INVENTION

The present invention, which solves the above problem, relates to a pharmaceutical composition comprising pharmaceutically active amounts of galanin, octreotide and serotonin, respectively, and a pharmaceutically acceptable carrier. Further a composition comprising galanin, octreotide and serotonin, for medical use is claimed. A method for treating a human or non-human animal with a disorder, or may potentially be affected by a disorder, associated with neoplastic cells, comprising the step of administering a composition as set out above is also disclosed.

DETAILED DESCRIPTION OF THE INVENTION

The pharmaceutically active components octreotide (which is a somatostatin analogue), galanin, and serotonin may be used in derivatized form or analogues thereof may be used as well. The above components may further be used in their salt forms.

According to one preferred embodiment of the present invention, the pharmaceutical composition, as set out in the present description, comprising pharmaceutically active amounts of galanin, octreotide and serotonin, respectively, and a pharmaceutically acceptable carrier provides an active dose lies in the range of from about 10 µg/kg body weight to about 60 µg/kg body weight of galanin, octreotide and serotonin, respectively; preferably about 10 µg/kg to about 20 µg/kg of galanin, octreotide and serotonin, respectively.

The expression "pharmaceutically acceptable" is meant to include in the present description ingredients that are compatible with other ingredients of the compositions as well as physiologically acceptable to the recipient, e.g. a human, without the production of undesirable physiological effects such as nausea, dizziness, gastric upset and the like. Compositions for use according to the present invention may comprise one or more carriers, excipients and/or diluents as set out below.

According to one preferred embodiment of the present invention there is provided use of a composition as set out above in the preparation of a medicament for the treatment, profylaxis or management of a disorder associated with neoplatic cells.

According to one preferred embodiment of the present invention there is provided a method for treating a human or non-human animal with a disorder, or may potentially be affected by a disorder, associated with neoplastic cells comprising the step of administering a composition comprising galanin, octreotide and serotonin. The disorder associated with neoplastic cells may e.g. be colorectal cancer, gastric cancer, prostate cancer, cancer in the pancreas. Preferably the disorder is colorectal cancer. Preferably the active dose lies in the range of from about 10 µg/kg body weight to about 60 µg/kg body weight of galanin, octreotide and serotonin, respectively; preferably about 10 µg/kg to about 20 µg/kg of galanin, octreotide and serotonin, respectively.

Non-human animals which may be treated preferably include mammals, particularly livestock and domestic animals such as dogs, cats, rabbits, guinea pigs, hamsters, mice, rats, horses, goats, sheep, pigs and cows.

Depending on the mode of administration, various forms of the compositions may be used. Thus, pharmaceutical compositions may be formulated in conventional manner using readily available ingredients. The active ingredients i.e. galanin, octreotide and serotonin may be incorporated, optionally together with other active substances, with one or more conventional carriers, diluents and/or excipients, to produce conventional galanic preparations such as tablets, pills, powders, lozenges, sachets, cachets, elixirs, suspensions, emulsions, solutions, syrups, aerosols (as a solid or in a liquid medium), ointments, soft and hard gelatine capsules, suppositories, sterile injectable solutions, sterile packaged powders, and the like.

Examples of suitable carriers, excipients and diluents, are lactose, dextrose, sucrose, sorbitol, mannitol, starches, gum acacia, calcium phosphate, alginates, tragacant, gelatine, calcium silicate, microcrystalline cellulose, polyvinylpyrrolidone, cellulose, water syrup, water, water/ethanol, water/glycol, water/polyethylene glycol, propylene glycol, methyl cellulose, methylhydroxybenzoates, propyl hydroxybenzoates, talc, magnesium stearate, mineral oil or fatty substances such as hard fat or suitable mixtures thereof. The compositions may additionally include lubricating agents, wetting agents, emulsifying agents, suspending agents, preserving agents, sweetening agents, flavouring agents, and the like. The compositions of the intention may be formulated so as to provide quick, sustained or delayed release of the active ingredient after administration to the patient by employing procedures well known in the art. Compositions may be in an appropriate dosage form, for example as an emulsion or in liposomes, niosomes, microspheres, nanoparticles or the like. If the target disorder is not present in the stomach, the composition comprising galanin, octreotide and serotonin according to the present invention and the composition is taken orally, said composition is enterically coated for passage through the stomach; enteric coatings as such are well known in the art. Examples of enteric coating polymers are cellulose acetate phtalate, hydroxy propyl methyl cellulose phtalate, polyvinyl acetate phtalate carboxy metyl ethyl cellulose, co-polymerized methacrylic acid and methacrylic acid/methacrylic acid methyl esters such as compounds known under the trade name Eudragit (Röhm Pharma).

If required, the compositions may also contain targeting moieties attached to the active ingredient, e.g. a ligand which binds specifically and selectively to an endogenous receptor to allow targeting to a particular cell type or location, such as targeting to certain specific e.g. vitally affected cells. Thus an even more targeted action may be accomplished.

Administration may be performed by local or systemic application as appropriate.

Administration of compositions for use in the invention may take place by, any of the conventional routes, e.g. by inhalation, orally, rectally or parenteraUy, such as by intramuscular, subcutaneous, intraarticular, intracranial, intradermal, intraocular, intraperitoneal, intrathecal, intravenous injection although this depends on the condition to be treated. The injection may even be performed directly into an affected locus (for example, by stereotaxic injection). Local administration may also be performed, e.g. at an affected site e.g. by use of a catheter or syringe. Treatment by topical application of a composition, e.g. an ointment, to the skin is also possible for appropriate conditions. Optionally administration may be performed at intervals, e.g. 2 or more applications, e.g. 2–4 applications at hourly, daily, weekly or monthly intervals, e.g. several times a day, or every 3–5 days, or at fortnightly, monthly or quarterly intervals.

The active ingredients i.e. galanin, octreotide and serotonin in compositions used in the invention may be comprised from about 0.01% to about 99% by weight of the formulation, preferably from about 0.1 to about 50%, for example 10%. The compositions may preferably be formulated in a unit dosage form, e.g. with each dosage containing from about 0.01 mg to about 1 g of the active ingredient, e.g. 0.05 mg to 0.5 g, for a human, e.g. 1–100 mg. The precise dosage of the active compound to be administered and the length of the course of treatment will, of course, depend on a number of factors including for example, the age and weight of the patient, the specific condition requiring treatment and its severity, and the route of administration. Generally however, an effective dose may lie in the range of from about 10 μg/kg body weight to about 60 μg/kg body weight of galanin, octreotide and serotoin, preferably about 10 μg/kg to about 20 μg/kg of galanin, octreotide and serotonin, respectively, per day, depending on the animal to be treated and the dosage form, taken as a single dose. Thus for example, an appropriate daily dose for an adult may be from 0.5 mg to 2 g per day, e.g. 1.0 to 500 mg of galanin, octreotide and serotoi respectively, per day.

As noted above, the present invention provides a variety of pharmaceutical compositions, such as also vaccine compositions against neoplastic cells.

We will now describe the present invention by using Figures and Examples but they are only for purposes of illustration and shall not in any way limit the scope of the appended set of claims.

FIGURE LEGENDS

FIG. 1 shows The effect of triple therapy with octreotide, galanin, and seroton on the tumour volume (A) and wet tumour weight (B). The tumour volume (C) and wet weight (D) in the mouse groups that received octreotide, galanin, or serotonin.

Figure 2:
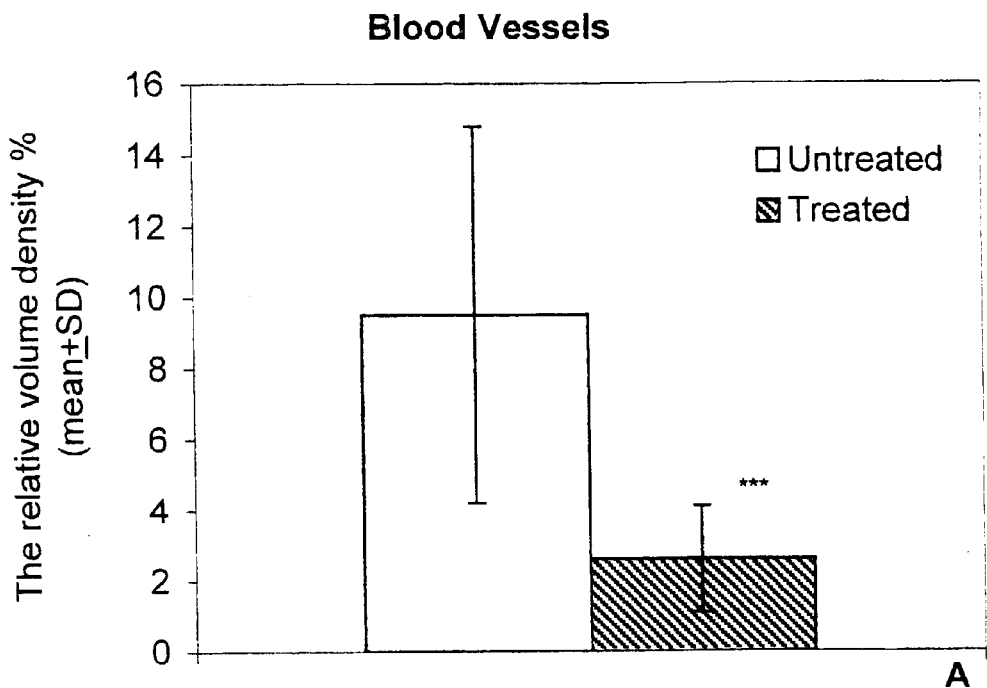
Figure 2:
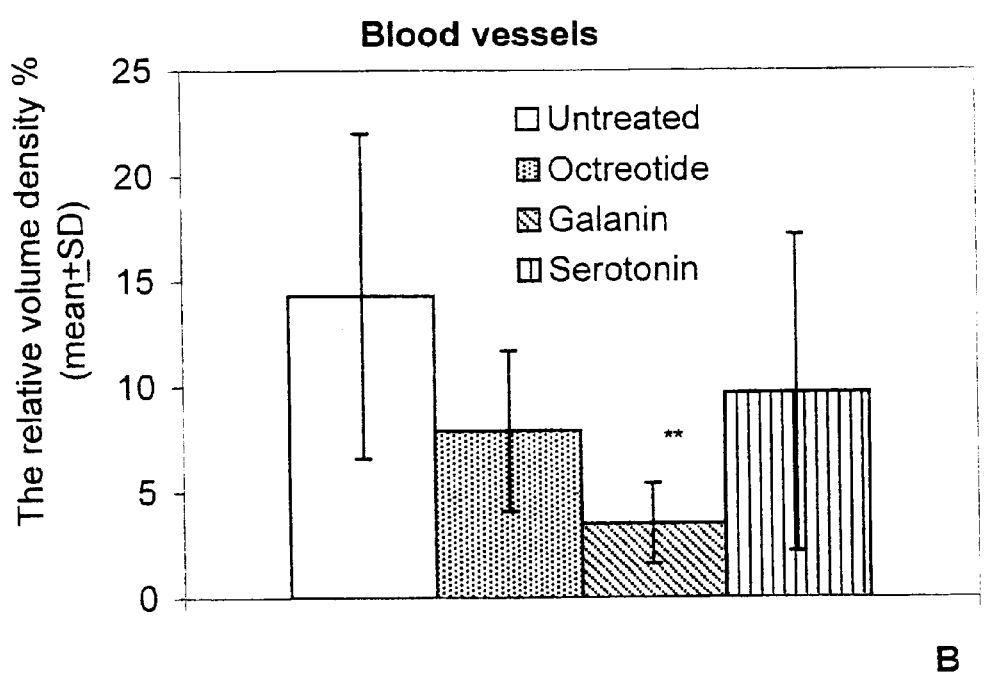

FIG. 2. shows the relative volume density of blood vessels with triple therapy (A) and with octreotide, galanin, or serotonin (B).

Figure 3:
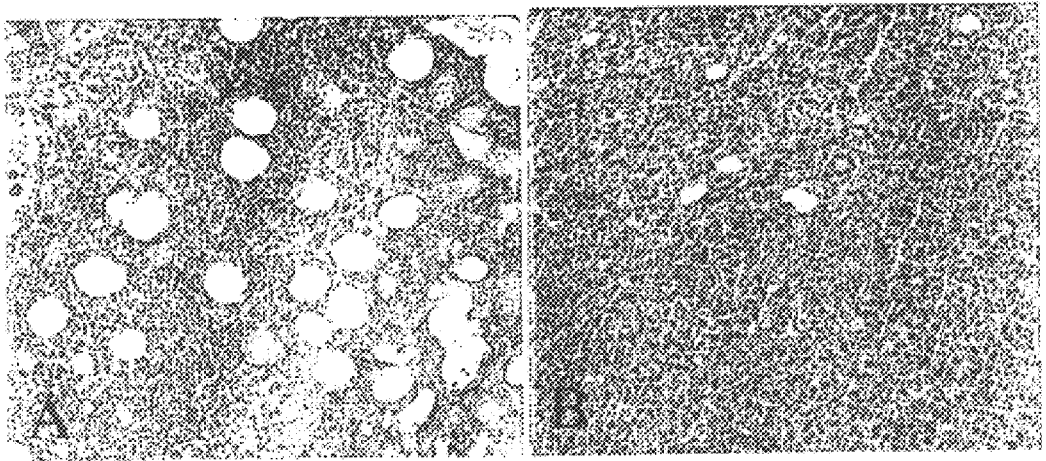

FIG. 3. shows the blood vessels in a tumour in a control mouse (A) and in a tumour in a mouse that received galanin (B). H&I. X85.

Figure 4:
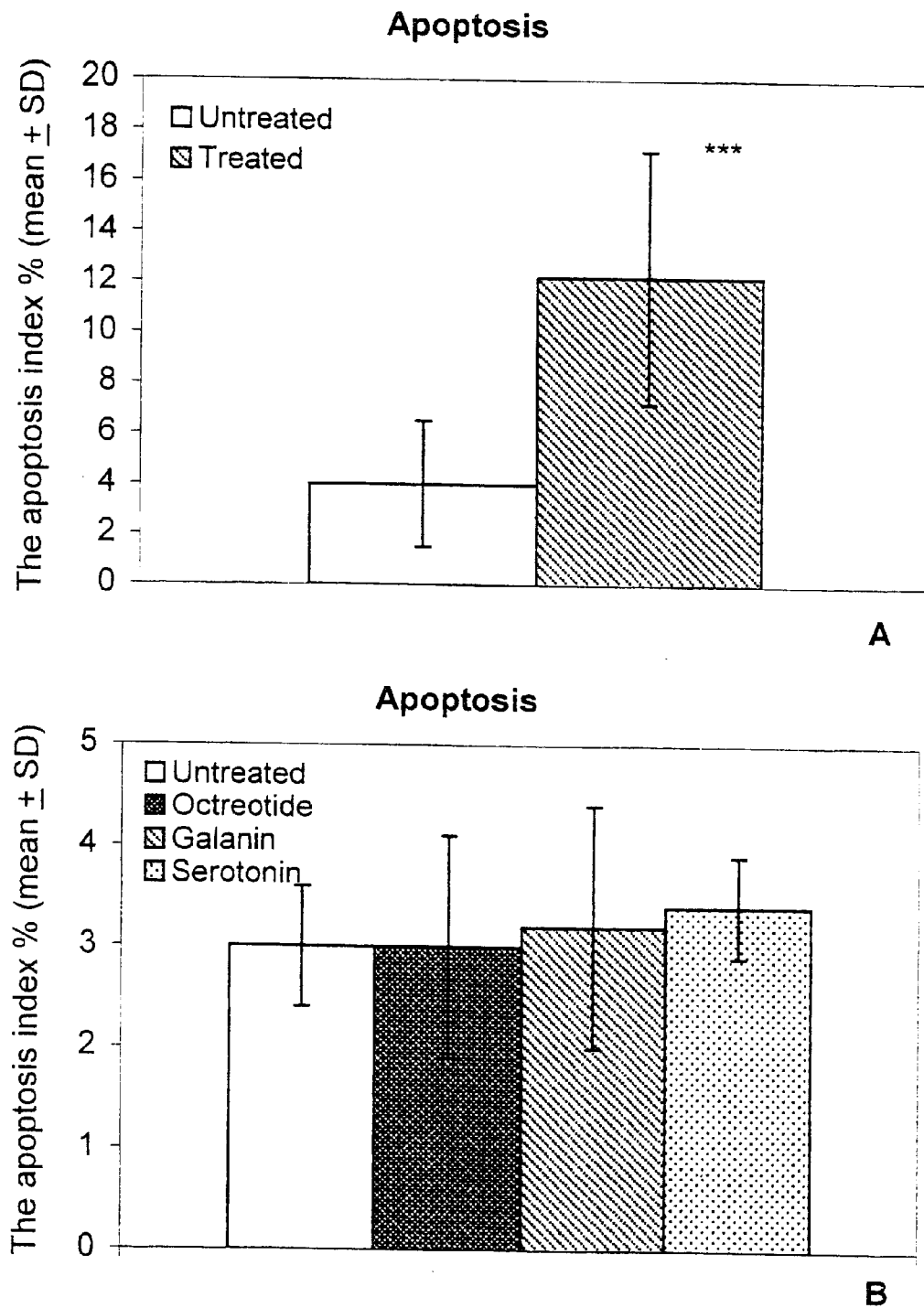

FIG. 4. shows apoptotic index in tumours with triple therapy (A) and in tumours treated with octreotide, galanin, or serotonin (B).

Figure 5:
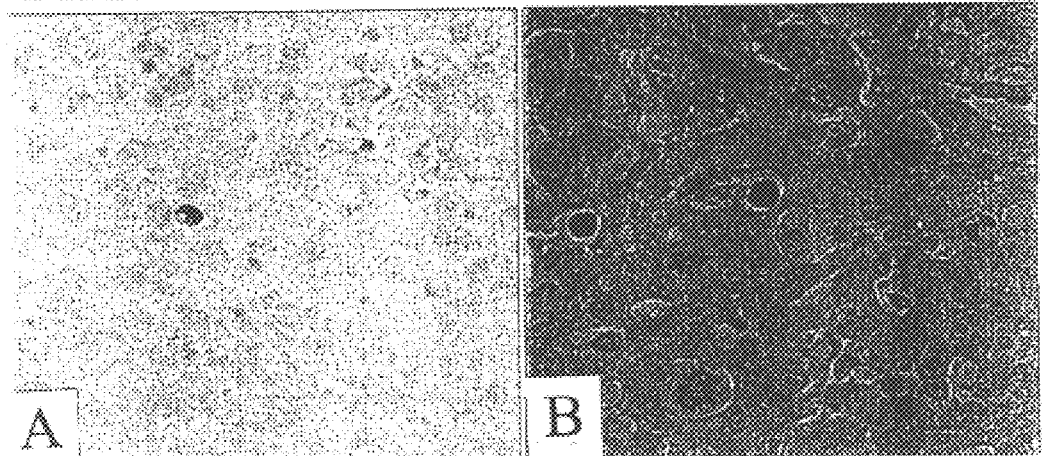

FIG. 5. shows apoptosis in a control tumour that received saline solution (A) and in a tumour treated with triple therapy. The nuclei with apoptosis stained brown. In situ hybridization. X400.

Figure 6:
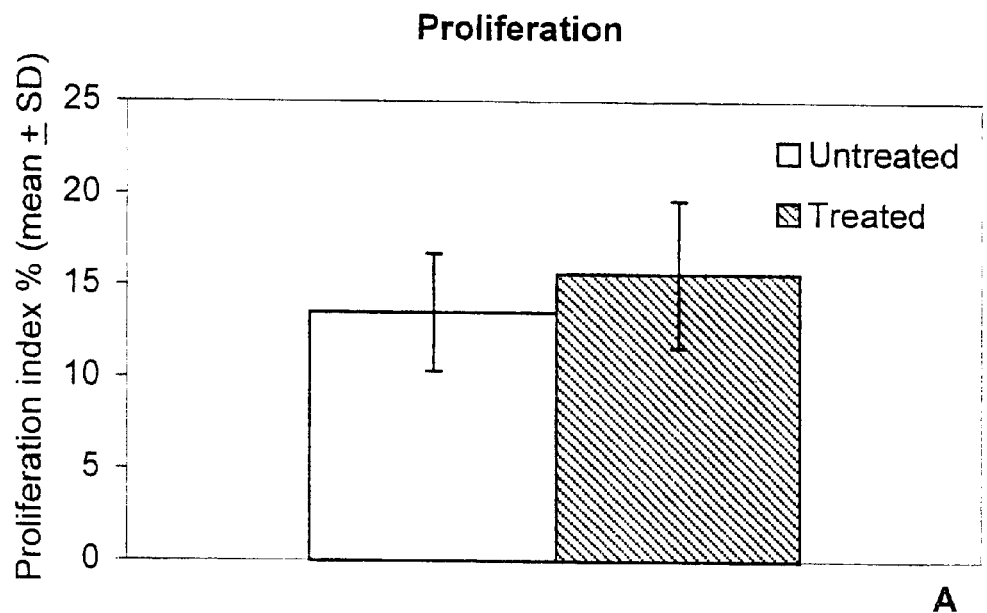
Figure 6:
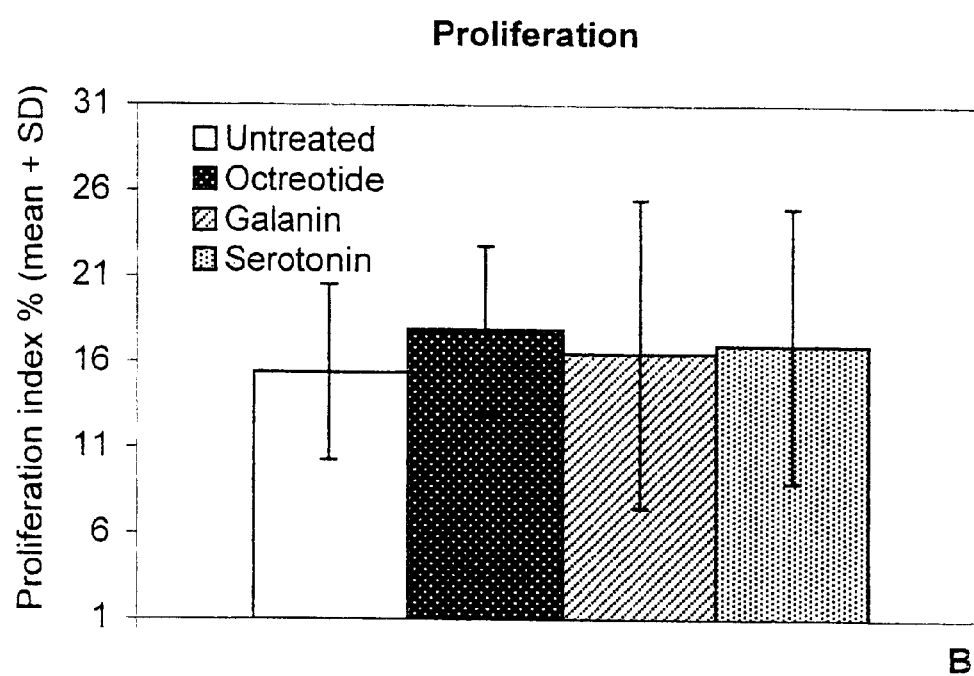

FIG. 6. shows the proliferation index in tumours with triple therapy (A) and in tumours treated with octreotide, galanin, or serotonin (B).

Figure 7:
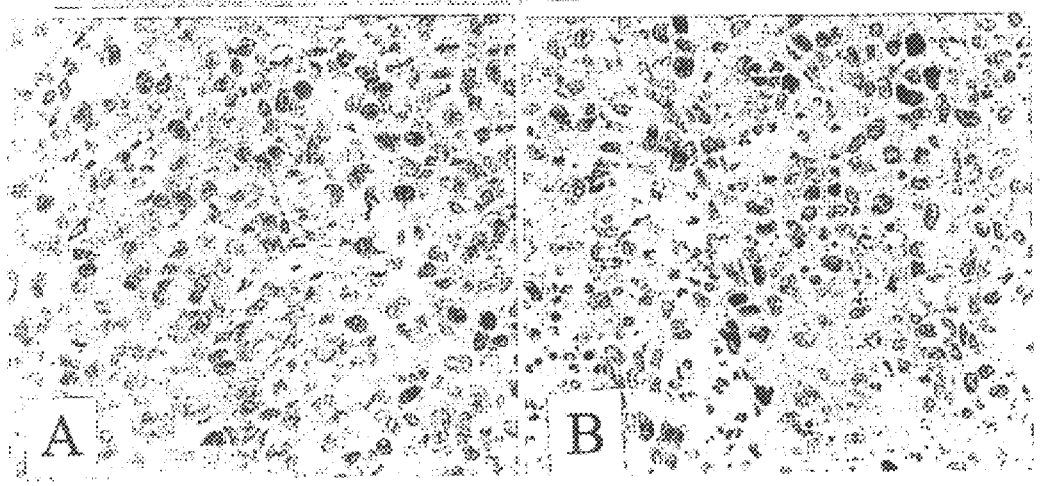

FIG. 7. shows proliferation in a control tumour (A) and in a tumour that received triple therapy (B). Proliferating nuclei stained brown. Avidin-biotin-complex method. X400.

Figure 8:
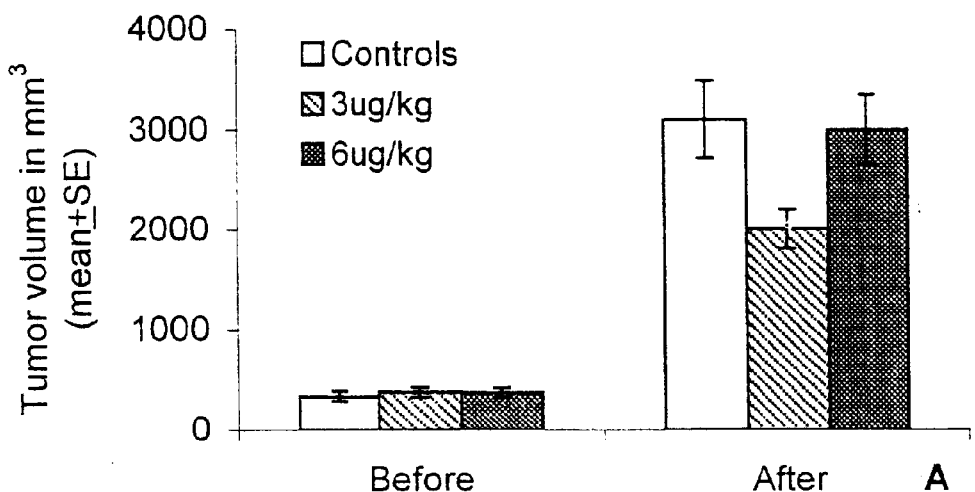
Figure 8:
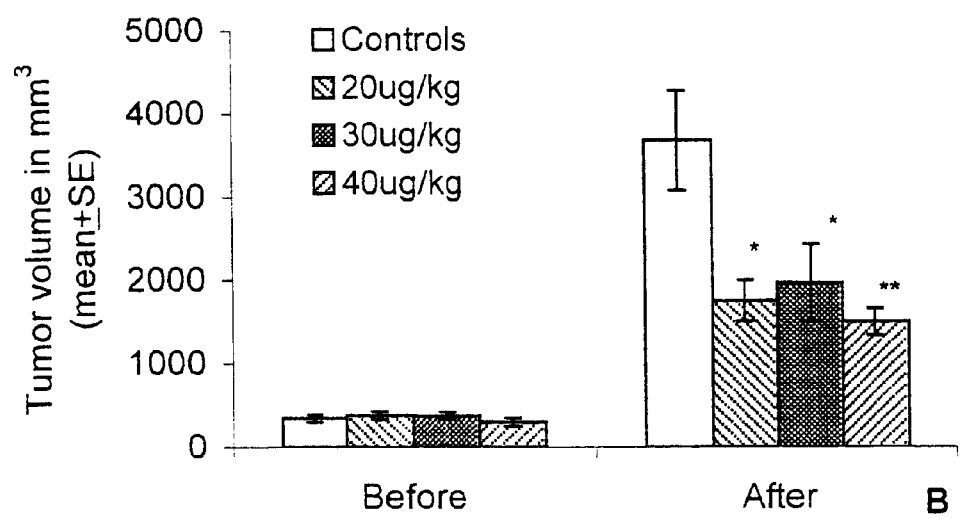

FIG. 8. shows the effect of 10w (A) and high dose (B) of triple therapy with octreotide, galanin and serotonin on the tumour volume.*=P<0.05; **=P<0.01.

Figure 9:
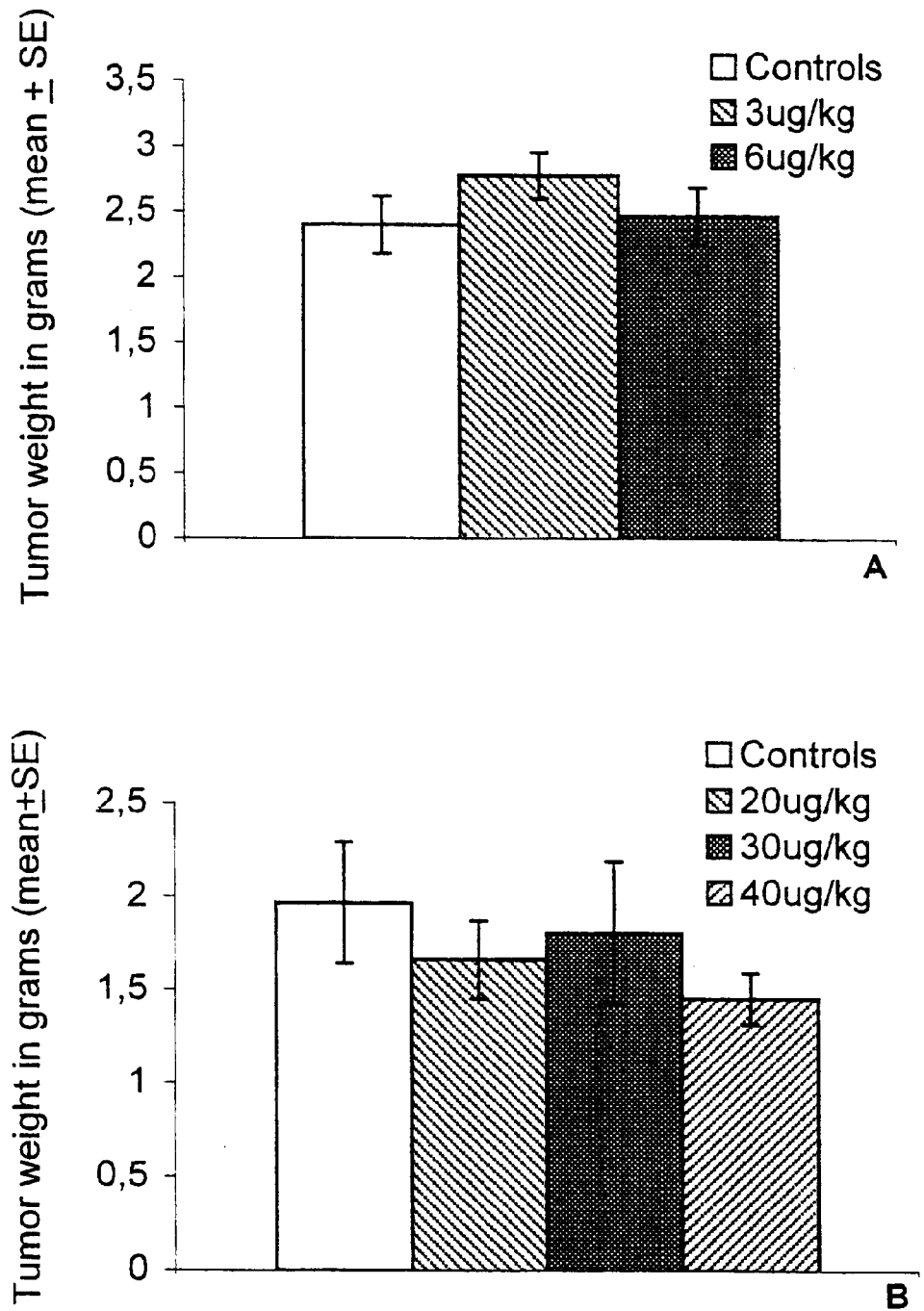

FIG. 9. shows the effect low dose (A) and high dose (B) of triple therapy with octreotide, galanin and serotonin on the tumour weight.

Figure 10:
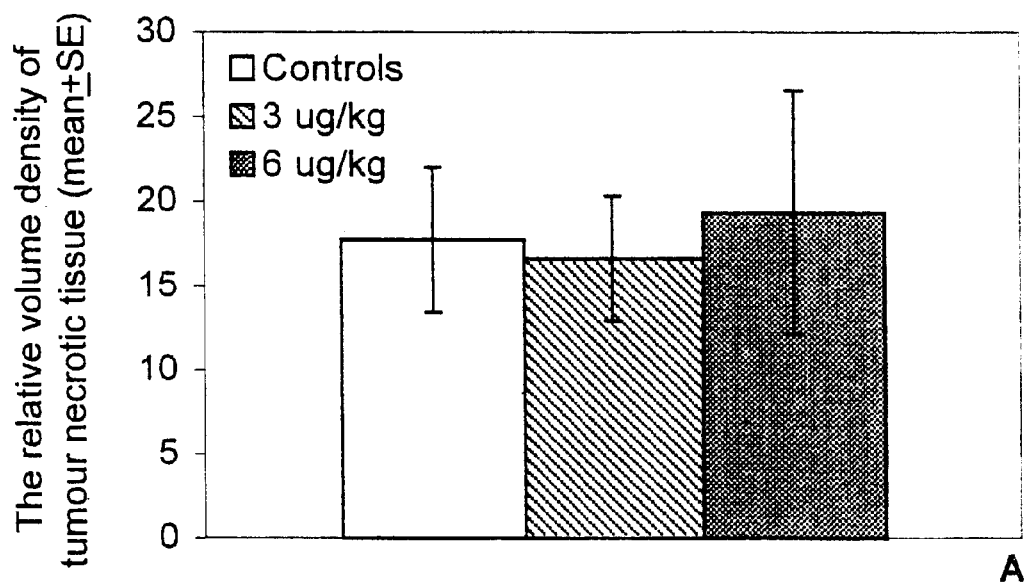
Figure 10:
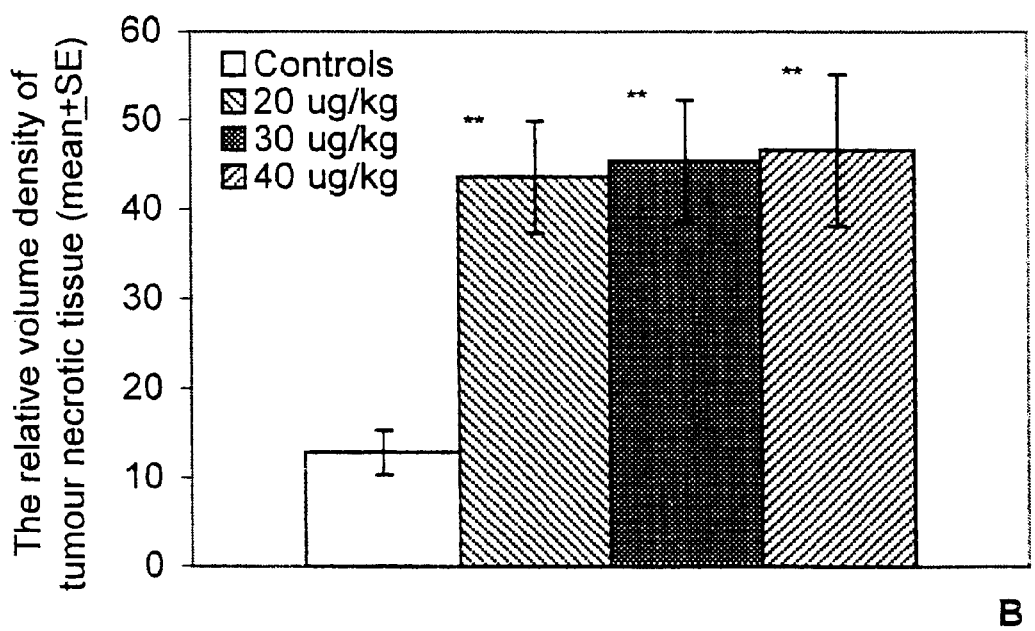

FIG. 10 shows the relative volume density (%) of necrotic tissue in the tumour in animals treated with low dose (A) and high dose (B) of octreotide, galanin and serotonin on the tumour weight. Symbols as in FIG. 9.

Figure 11:
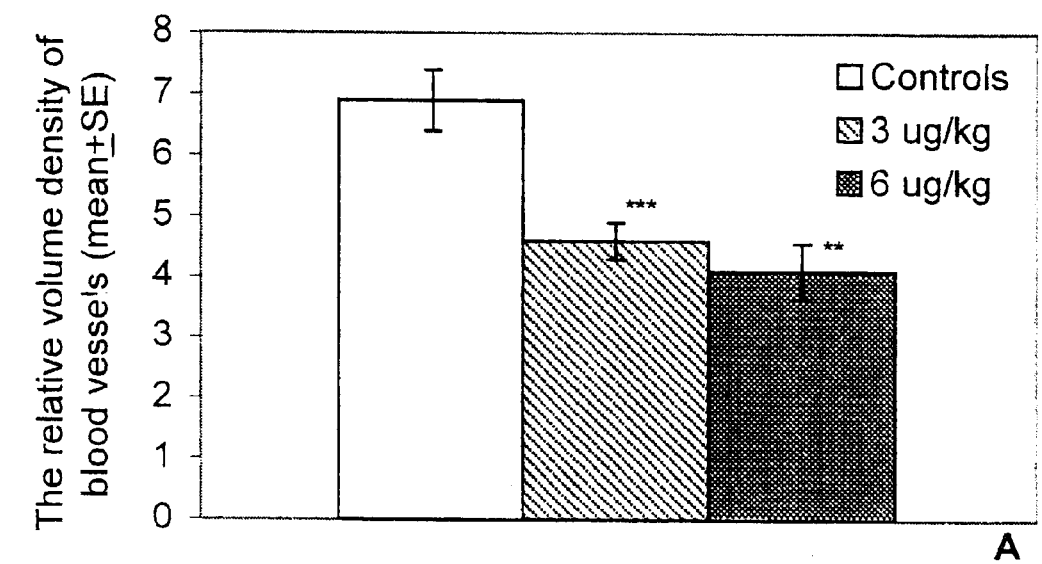
Figure 11:
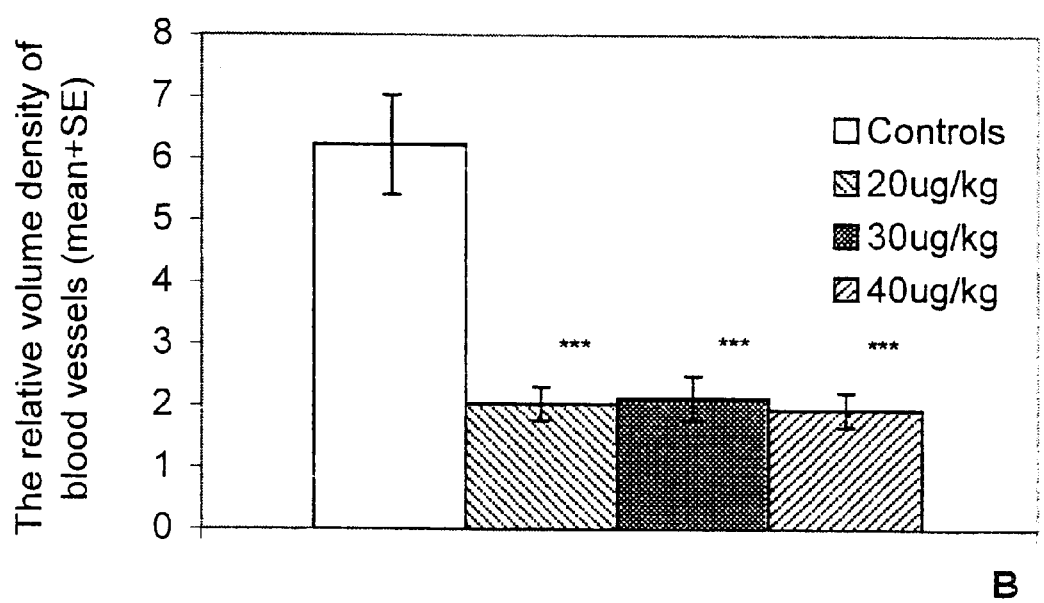

FIG. 11. shows the relative volume density (%) of tumour blood vessels in tumour treated with low dose (A) and high dose (3) of octreotide, galanin on serotonin. ***=P<0.001. Symbols as in FIG. 8.

Figure 12:
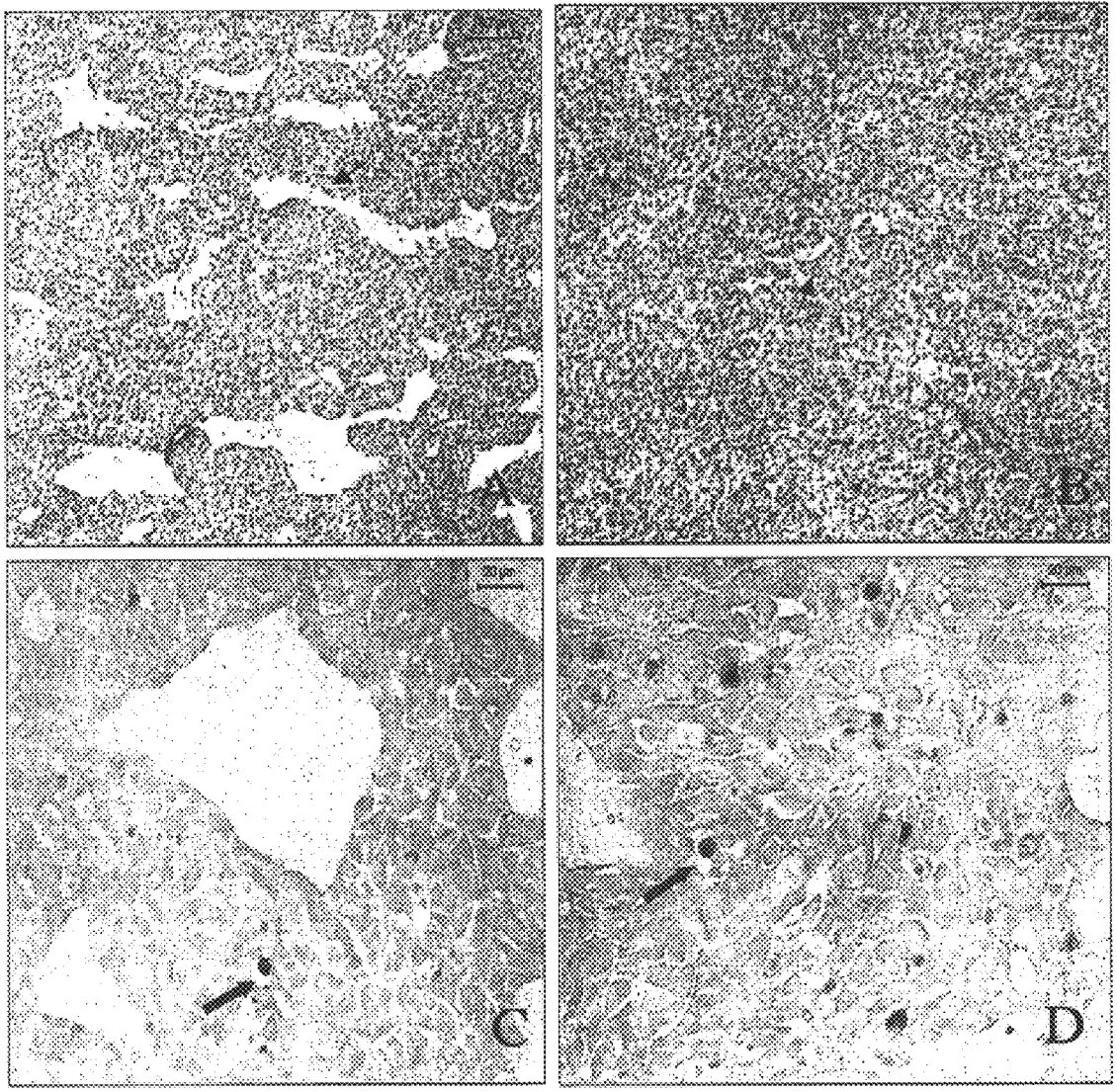

FIG. 12. shows the blood vessels in a tumour in a control mouse (A) and in a tumour in a mouse 20 μg/kg body weigh triple therapy (B). Apoptosis in a tumour in a control mouse (C) and in a tmnour in a mouse received 20 μg/kg body weigh triple therapy (D).

Figure 13:
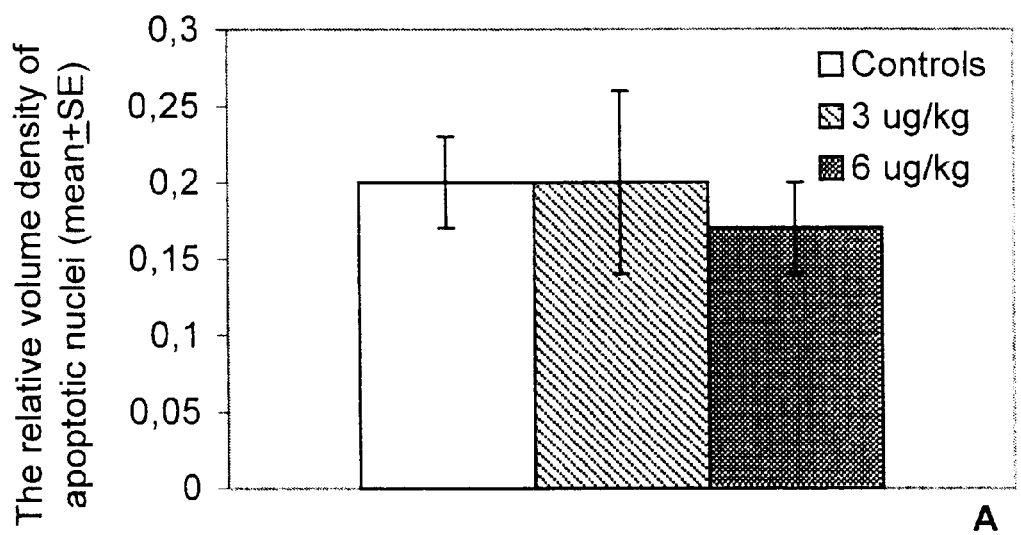
Figure 13:
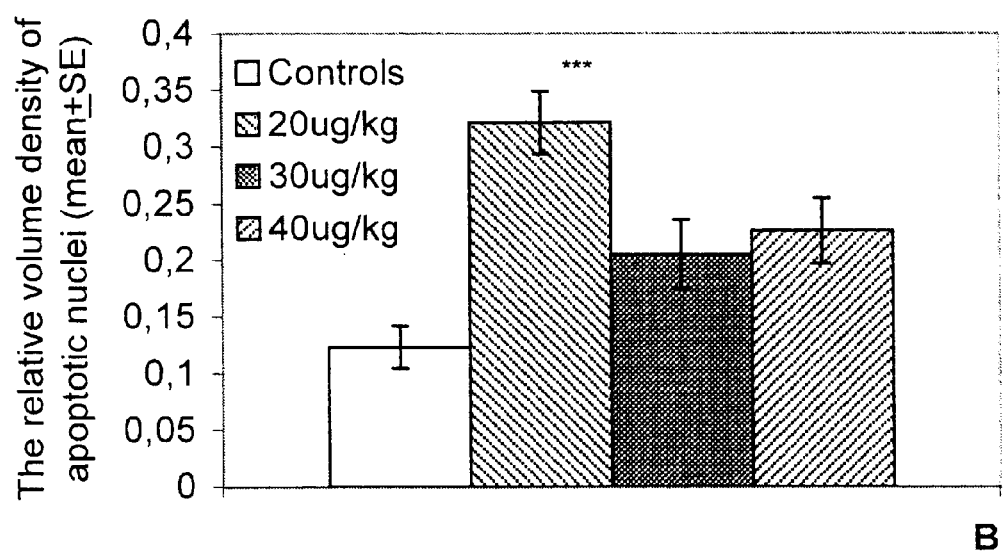

FIG. 13. shows the relative volume density of apopotic nuclei in tumours received low dose (A) and high dose (B) triple therapy (A). Symbols as in FIG. 11.

Figure 14:
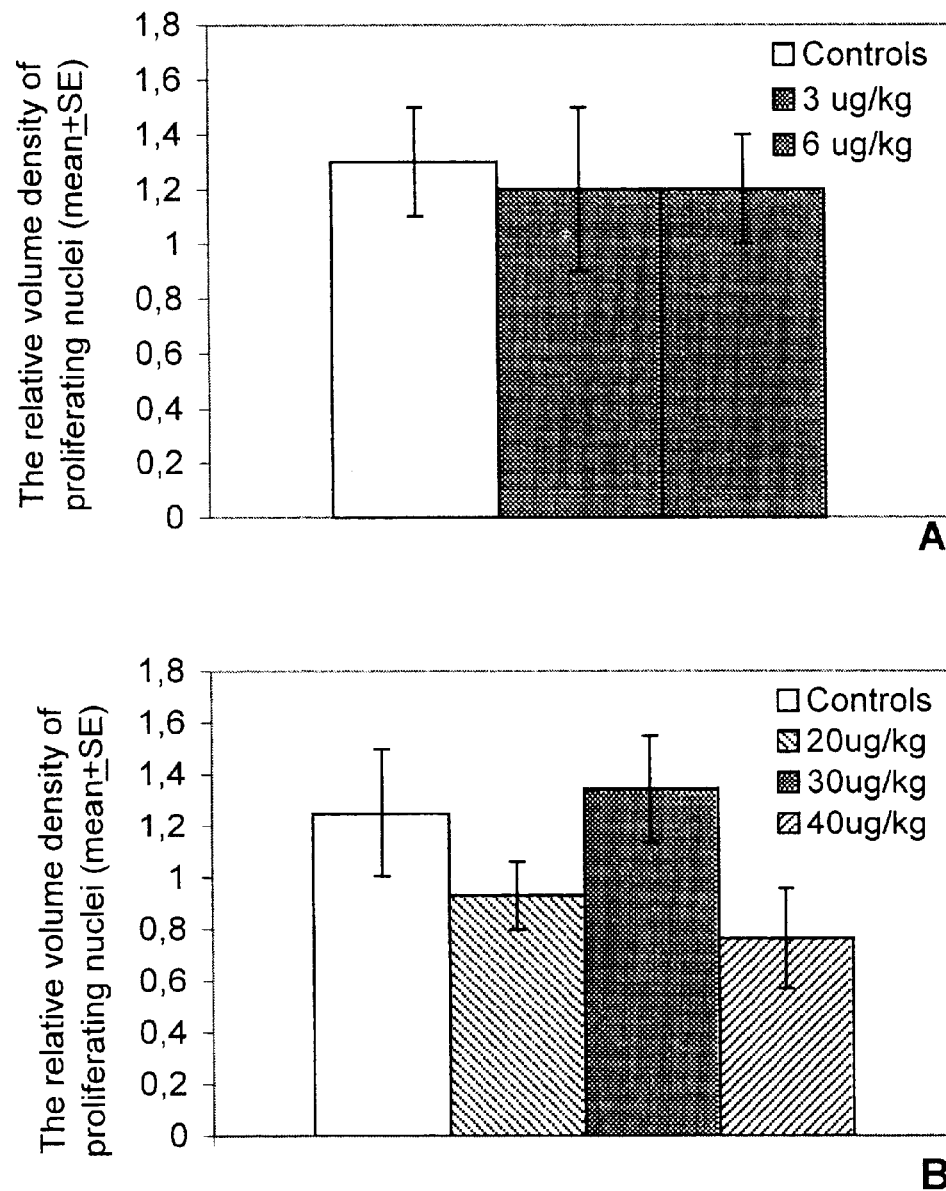

FIG. 14. shows the relative volume density of proliferating nuclei in tumours treated with low dose (A) and high dose (1) triple therapy.

EXAMPLES

Example 1

To summarize the first example, a rat colonic adenocarcinoma was implanted subcutaneously in female nude (C57BL/6JBom-nu) mice. After seven days, the animals were divided into different groups. One group received triple therapy with octreotide, galanin, and serotonin, 10 μg/kg body weight of each, twice daily. Three groups received 10 μg/kg body weight twice daily of either octreotide, galanin, or serotonin. The last group consisted of controls that received only saline solution. The treatment lasted for five days. The tumour volume, wet weight, and relative volume density of blood vessels were significantly decreased after the triple treatment, as compared to controls. Apoptotic index was significantly increased, but the proliferation index was not affected in the group of mice that received triple therapy. There was no significant difference between controls and mice treated with octreotide, galanin, or serotonin regarding tumour volume or weight. The relative volume density of blood vessels was decreased in tumours treated with galanin, but not with octreotide or serotonin. There was no statistical difference in the proliferation index between controls and animals treated with ether octreotide, galanin or serotonin, as compared with controls. Tumour necrosis and increased apoptosis maybe responsible for the reduction in the volume and weight of the tumour after triple therapy. Tumour necrosis may be caused by the induction of tumour ischemia due to a reduction in tumour blood flow, which is caused by decreased incidence of tumour-feeding blood vessels, and by constriction of tumour-feeding arterioles. These results suggests a new and improved treatment for colon cancer as set out in the present description.

Material and Methods

Animals

Female nude mice (C57BL/6JBom-nu, Bomholtgård Breeding and Research Centre, Denmark), 8 weeks old, with a mean body weight of 22.9 g (range 20.4–25.5), were used in this investigation. The mice were kept one to each cage in a laminar filtered airflow cabinet under pathogen-free conditions. The animals were kept under a constant temperature (22±2° C.) and relative humidity (55±5%), with 12 h dark/light cycles. They were fed on a standard pellet diet (R 34, Lactamin, Vadstena, Stockholm) and given water ad libitum. All experiments were performed by aseptic techniques under laminar airflow.

Tumour Implantation and Treatment

Twenty mice were injected s.c. with 100 μl cell suspension containing 2×10$^6$ viable cells of an N-methyl-N'-nitroguanidine-induced rat colonic adenocarcinoma (provided kindly by Professor L.-O. Hafström, Department of Surgery, University Hospital, Umeå, Sweden). After seven days, the greatest and least diameters of the tumours were measured and the volume was calculated with the use of the following formula:

$$\text{volume} = (\text{mean diameter})^3 3 \pi/6.$$

The animals were divided into two groups of 10 mice each. The first group received s.c. injections of 100 μl saline solution containing a mixture of octreotide (Sandostatin®, Novartis), galanin (synthetic human galanin, Sigma, Stockholm), and serotonin (5-hydroxytryptamine, oxalate salt, Sigma) at 10 μg/kg body weight each. Injections were administered every 12 hours for five days. The second group served as controls and received only saline solution. Thirty-two mice were implanted with the tumour as described above and left for seven days. After measuring the tumour diameter, the animals were divided into four groups of eight. The first group was injected with 100 μl saline solution, the second with 100 μl saline solution containing 10 μg/kg body weight octreotide, the third group with 100 μl saline solution containing 10 μg/kg body weight galanin, and the last group was injected with 100 μl saline solution containing 10 μg/kg bodyweight serotonin. Injections were administered every 12 hours for five days.

At the end of the experiments, the animals were weighed and then decapitated. The tumours were dissected carefully and their diameters and weight were determined. Three tissue samples cut perpendicular to the surface were taken from each tumour, two from the periphery and one from the middle. The tissue samples were fixed overnight in 4% buffered paraformaldehyde, embedded in paraffin wax, and cut at 5 μm.

Blood Vessel Density

The slides were coded, as in all the subsequent morphometeric analyses, and the performer was not aware of the identity of the sections. The sections were stained with haematoxylin-eosin. In order to determine the relative volume density of the blood vessels, a classic stereological point-counting was used (Weibel and Elias, 1967; Weibel et al, 1969). Briefly, a regular square 121-point lattice was inserted in the eye piece of the microscope and examination was done with an ocular X12.5 and an objective X10. Thirty fields were randomly chosen from each tumour; 10 from each tissue sample. Points covering blood vessels were counted and related to points covering the tumour tissue.

Apoptasis

Apoptosis was detected by in situ hybridisation using two different kits (TA200 and TA5411) from R&D Systems Inc (Minneapolis, Minn. USA). Both kits detect DNA fragmentation, but with two different detection approaches. In the first kit, fragments of DNA were detected by incorporating modified nucleotides at the 3'OH ends of the fragments, using terminal deoxynucleotidyl transferase (TdT). The incorporated 5-bromodeoxyuridine (BrdU) was detected by a biotinylated anti-BrdU antibody. A streptavidin-conjugated horsradish peroxidase specifically bound to the biotinylated antibody. In the second kit, TdT added biotinylated nucleotides to the 3'OH ends of the DNA fragments. Again, a streptavidin-conjugated horseradish peroxidase specifically bound to the biotinylated DNA fragments. The peroxidase in both kits was detected by diaminobenzidine tetrahydrochloride (DAB). The sections were counter-stained with methyl green. The in situ hybridisation was performed according to the protocol supplied by the manufacturer. Controls included nuclease-generated positive controls; unlabelled sample controls and labelled untreated sections from normal tissue (mouse colon).

Apoptotic index was determined using the unbiased counting frames (as described in detail previously), adapted to computer image analysis (Palmqvist et al., 1998). The image processing and analysis system used was Quantimet 500MC (Leica, Cambridge, England) linked to an Olympus microscope, type BX50. The program used in this system was QWIN (Leica's Windows-based image analysis tool kit, version 1.02). In addition, the system included QUIPS (version 1.02), an interactive programming system. Briefly, a frame (field) was created with an area of 3690 □m$^2$ in the computer monitor. About 40 fields from each tumour, spread randomly in sections from the three tissue samples, were measured. For each tumour about 200 positive and 200 negative nuclei were counted. The labelling index (LI) was calculated as follows:

$$LI=(P/A_1)/N/A_2+P/A_1$$

Where P is the number of positive nuclei, $A_1$ is the area of the counting frame used to count positive nuclei, N is the number of negative nuclei and $A_2$ is the frame area used for counting the negative nuclei.

Proliferadon

To detect proliferation, the sections from the tumour tissue samples from all the animals were immnmostained with the avidin-biotin-complex (ABC) method (Dakopatts, Glostrup, Denmark), as described in detail earlier (E1-Salhy et al., 1993). Briefly, the sections were immersed in 0.5% $H_2O_2$ in Tris-buffer, pH 7.6, for 10 min, to block the endogenous peroxidase. They were then incubated with 1% borine serum albumin for 10 min to occupy the non-specific binding sites. The sections were incubated with primary antibodies for 20 h at room temperature. The primary antibodies used were Proliferating cell nuclear antigen (PCNA) (monoclonal, code number M0879, dilution 1:50, Dakopatts), purified anti-hunan Ki-67 antigen (monoclonal, code number M7187, dilution 1:50–1:1 000, Dakopatts), and affinity isolated anti-human Ki-67 antigen (polyclonal, code number A0047, dilution 1:50–1:1 000, Dakopatts). Incubation with the secondary antibody, biotinylated swine anti-rabbit or anti-mouse IgG, diluted 1:200, was carried out at room temperature for 30 min. The sections were then incubated for 30 min with the avidin-biotin-peroxidase complex, diluted 1:200, at room temperate. Peroxidase was detected by immersing the sections in 50 ml Tris-buffer containing 25 mg diaminobenzidine tetrahydrochloride (DAB) and 10 µl of 30% $H_2O_2$ followed by slight counter-staining in Mayer's haematoxylin. Specificity controls included negative controls and positive controls. As a negative control, the sections were incubated with non-immune serum instead of the primary antibodies. Positive controls included immunostaining of sections from human colon adenocarcinoma. The proliferating index was determined as described for apoptosis.

Statistical Analysis

Comparison between two groups was performed with the Wilcoxon non-paratetric test. Comparison between four groups was done with Krukskal-Wallis non-parametric ANOVA test and Dunn's multiple comparisons was used as a post-test. P values below 0.05 were considered significant.

Results

The animals seemed to feel well during the experiments. Two mice in the group treated with galanin died. Dissection of these mice showed that one had metastasis in the liver and regional mesenteric lymph nodes, while the other had abdominal carcinosis.

Tumour Diameter and Weight

Tumour volume and wet weight were significantly decreased after the triple treatment with octreotide, galanin, and serotonin, as compared to controls (P=0.03 and 0.02, respectively). There was no significant difference between controls and mice treated with octreotide, galanin, or serotonin, regarding either tumour volume or weight (P=0.4 and 0.8, respectively) (FIG. 1).

Blood Vessel Density

The relative volume density of blood vessels in the tumours in the group treated with triple therapy was significantly decreased as compared to controls (P=0.0002). There was a significant difference/between controls and octreotide, galanin-, and serotonin-treated mice (P=0.01). Post-test results showed that the relative volume density of blood vessels was decreased in tumours treated with galanin vs. controls (P<0.01) (FIGS. 2 and 3).

Apoptosis

Apoptotic index was significantly higher in the animal group that received triple therapy (P=0.0004) using the first in situ hybridisation kit (FIGS. 4 and 5). The Apoptotic index in mice that received triple therapy using the second kit was 13.4±5.1 (mean±SD). The corresponding figures for controls were 4.5±1.8. The difference between treated animals and controls was also statistically significant (P=0.0003). Using the first in sit hybridisation kit, there was no difference between the controls and the animal groups treated with octreotide galanin, or serotonin (P=0.2) (FIG. 4). Use of the second in situ hybridisation kit in groups treated with octreotide, galanin, and seroton resulted in apoptotic indexes of 3±1.1, 4±1.2, and 4±0.5 (mean±SD), respectively. The corresponding figures for controls were 3.5±0.6. There was no statistical significance between the treated groups vs. controls (P=0.15).

Proliferation

The results of the motpbometeric analysis are presented in FIG. 6 and illustrated in FIG. 7. There was no statistical difference regarding the tumour proliferation index (P=0.2) between controls and animals that received triple therapy. Neither was there any difference between animals treated with octreotide, galanin, or serotonin, as compared with controls (P=0.8). Immunostaining with anti-human Ki-67 antigen did not yield any immunostaining.

Discussion

The present study showed that five days triple therapy with octreotide, galanin, and serotonin significantly reduced the volume and weight of a rat colonic adenocarcinoma Tumour necrosis and increased apoptosis may be responsible for this reduction in tumour volume and weight. Tumour necrosis may be caused by the induction of tumour ischemia due to a reduction in tumour blood flow, which results from decreased tumour-feeding blood vessels, and by the constriction of tumour-feeding arterioles caused by serotonin (Laemel et al., 1998). The present triple therapy did not affect tumour cell proliferation. The effect of the triple therapy seems therefore to be caused by the detection of the tumour cells. Most chemotherapy drugs, such as fluropyrimidines, ralti trexed, and platinum-based agents, are growth-regulating; they reduce growth, but do not cause death of tumour cells. This would suggest that this therapy could be combined with any of the previously mentioned drugs to enhance and increase the treatment effect. None of the bioactive substances given alone affected tumour volume or weight, indicating that octreotide, galanin, and serotonin exert a synergetic effect.

Several studies using various gut neuroendocrine signal substances and their antagonists have been carried out over the past few years (Windsett et al., 1986; Smith and Solomon 1988; Alonos et al. 1990; Narayan et al., 1990; van-Tol et al., 1991; Gamet et al., 1992; Qin wt al, 1992; Yoshinaga et al, 1992; Radulovic et al., 1994; Smith et al., 1994 Goldberg et al., 1995; Robinbins, 1996). The present study, however, differs fundamentally from these studies; whereas the previous studies were initiated fom the expected pharmacological effect of these substances on colon carcinoma, in the present study, a substitution of the gut bioactive signal substances, found to be low in patients with colorectal carcinoma, was made.

Somatostatin and somatostain analogues have been reported to inhibit the proliferation of human and rat colon cancer cells, both in vitro and in vivo (Smith and Solomon, 1986; Alonos et al., 1990; Qin et al., 1992; Radulovic et al., 1994; Robbins, 1996). Clinical trials using a somatostatin analogue, octreotide, have been disappointing (Goldberg et al., 1995). This is due to the fact that the high doses used in experimental studies were not tolerable for patients and caused severe diarrhea and abdominal pain. In a clinical trial, patients with asymptomatic advanced colon carcinoma were treated with octreotide, with about 7 $\mu$/kg/d having had no effect on the progression of the disease (Smith et al., 1994; Goldberg et al, 1995). In the present study, a similar low dose of octreotide (10 $\mu$g/kg) did not affect the turnout volume or weight, or the proliferation index.

In two studies from the same group, serotonin has been found to increase the mitotic rate of rat colonic cancer cells, while serotonin antagonists inhibit the growth of human colonic cancer in xenografts (Tutton and Barka, 1978; Barka and Tutton, 1981). Other studies from different laboratories have shown, however, that serotonin is involved in the induction of tumour ischemia by selective reduction of tumour blood flow through the constriction of tumour-feeding arterioles (Laemel et al., 1998; Baguley et al., 1993; Hunt and Lubbe, 1995; Baguley et al, 1997). In the present study, serotonin alone did not significantly affect tumour volume or weight, nor reduce the tumour blood vessels' relative volume density. However, in combination with octreotide and galanin, it had a marked effect on the tumour size and on the apoptotic index, indicating that serotoriin has an anti-tumour effect.

The effect of galanin on colon carcinoma has not, to the best of our knowledge, been investigated previously. It has been reported, however, that treatment with galanin significantly decreased the incidence of chemically induced colon cancer in rats (Lishi et al., 1995). The authors speculated that this effect might be due to the inhibition of the release of neurohormonal substances, such as vasoactive intestinal peptide (VIP) and neurotensin that are closely related to the development of colon tumours. In the present study, gallant's effect on colon carcinoma seemed to be exerted through inhibiting the formation of new blood vessels to the tumours, probably leading to ischemia and tumour cell necrosis.

The present study showed that triple therapy with octreotide, galanin, and serotonin decreases the volume and weight of rat colon carcinoma through inhibiting the formation of tumour-feeding blood vessels and increasing tumour cell apoptosis. Though these results are promising and may offer a treatment for of colon cancer, one must keep in mind that the most effective tolerable dose and combination must be determined. Furthermore, more tumours should be examined, especially human colon carcinoma, as colon carcinoma show heterogeneity in their response to different therapies. While it is certainly still a long way from certain what use the present findings will be in the treatment of patients with colorectal cancer, the present results are most encouraging and justify further investigations which can be seen in example 2 below.

Example 2

To summarize example 2 A rat colonic adenocaciuom was implanted subcutaneously in nude mice. After 7 days, the animals were divided into different groups. Two groups received subcutaneous injections twice daily with 3 or 6 $\mu$g/kg body weight octreotide, galanin and serotonin. Three groups were treated with 20, 30 or 40 $\mu$g/kg body weight of the previously mentioned bioactive substances. Control group received only saline solution in the same fashion as treated animals. The treatment lasted for 5 days. The tumour volume and weight, the relative density of blood vessels, of tumour necrotic tissue, of apoptotic nuclei and of proliferating nuclei were measured. Apoptosis was detected by in situ hybridisation, and proliferation by immunocytochemistry. Morphometry was done with the classical stereological point-counting method. Food consumption, animal weight, faeces weight and its water content were measured for 3 days before and after treatment. Triple therapy with 3 and 6 $\mu$g/kg body weight had no effect on any of the parameters measured, except in reducing the relative volume density of tumour blood vessels. Treatment with 20, 30 and 40 $\mu$g/kg body weight of the previously mentioned bioactive substances reduced the tumour volume, the relative volume density of blood vessels and increased the relative volume density of necrotic tissue and of apoptotic nuclei (in 20 $\mu$g group). But there was no difference between treated mice and controls regarding the relative volume density of proliferating nuclei, There was no statistical difference between treated animals regarding food consumption, body weight, faces weight and its water content before and during treatment. The present study confirms that triple therapy with octreotide, galanin and serotonin causes regression of a rat colon carcinoma. It further showed that optimum treatment dose is between 10–20 $\mu$g/kg body weight of each bioactive substance. Moreover, this therapy regime does not show apparent side-effects in the experiments carried out on mice.

Introduction

The neuroendocrine peptides and amines of the gut are involved in regulating the proliferation and growth of gastrointestinal epithelial and mesenchymal cells (1). They also regulate the local immune-defence of the gut (2). Both cell proliferation and local-immune defence of the gut are important factors for the development and growth of colorectal cancer. It is possible that an abnormality in the neuroendocrine system occurs in the colon of patients with colon carcinoma that might initiate and/or promote the development of the colorectal carcinoma (3). In support of this assumption are the findings of low levels of somatostatin and galanin, and the low number of colonic somatostatin and serotonin cells in patients with colon carcinoma (3,4). Moreover, the number of somatostatin and serotonin cells in the colon is restored in patients with rectal carcinoma that received preoperative radiotherapy (5). As pre-operative radiotherapy has been found to improve the 5- and 10-year survival rates and reduce local recurrences, it seems therefore that restoring of the number of these endocrine cells in these patients plays a role in improving their prognosis.

In a recent study from our group (6), the effect of triple therapy with octreotide, galanin and serotonin on rat colonic adenocarcinoma xenografs to nude mice was investigated. This study showed that 5 days of triple therapy reduced about 50% of the volume and weight of rat colon carcinoma. Increased tumour necrosis and apoptosis have been suggested to be responsible for this reduction. Tumour necrosis has been assumed to be caused by the induction of tumour ischemia by the reduction in tumour blood flow resulting from the decreased new formation of tumour-feeding blood vessels, and by constriction of tumour-feeding arterioles. Tumours treated with octreotide, galanin or serotonin alone showed no effect on the tumour volume or weight. Apart from the reduction of relative volume density of tumour blood vessels in tumours treated with galanin, there was no effect of single therapy with these bioactive substances on apoptotic or proliferation labelling indices. The authors concluded that these substances work in a synergetic fashion. In this earlier study (6), 10 $\mu$g/kg body weight of octreotide, galanin and serotonin were used. It has been thought that it would be of interest to test the effect of lower and higher doses of these bioactive substances on the same rat colon carcinoma. Thus, the present study was undertaken to investigate the effect of different doses of triple therapy with octreotide, galanin and serotonin. Furthermore, We possible side-effects of this treatment such as emesis, declined appetite and body weight diarrhea or constipation as well as mouse well-being were studied.

Methods—Animals

Female nude mice (C57BL/6JBom-nu, Bomholtgård Breeding and Research Centre, Denmark), seven weeks-old with a mean body weight of 18.7±0.5 g (mean±SD)), were used in this investigation. The mice were kept one to each cage in a laminar-filtered airflow cabinet under pathogen-free conditions. The animals were kept under a constant temperature (22±2° C.), and relative humidity (55±5%) with 12 h dark/light cycles. They were fed on a standard pellet diet (R 34, Lactamin, Vadstena, Stockholm) and given water ad libitum. All experiments were performed by aseptic techniques under laminar airflow. The animals were inspected daily and any sign of pain, or discomfort was recorded. The local committee on animal ethics at Umeå University approved the investigation.

Tumour Implantation and Treatment

Thirty mice were injected S.C. with 100 $\mu$l cell suspension containing $2 \times 10^6$ viable cells of an N-methyl-N'-nitroguanidine-induced rat colonic adenocarcinoma (provided kindly by Professor L.-O. Hafström, Department of Surgery, University Hospital, Umeå, Sweden). After seven days the greatest and least diameters of the tumours were measured and the volumes were calculated with the use of the following formula: volume=(mean diameter)$^3 \times \pi/6$. The animals were divided into three groups of 10 in each. The first control group was injected with 100 $\mu$l saline solution, the second with 1001 saline solution containing 3 $\mu$g/kg body weight octreotide (Sandostatin®, Novartis), galanin (synthetic human galanin, Sigma, Stockholm, Sweden) and serotonin (5-hydroxytryptamine, oxalate salt, Sigma). The third group was injected with 100 $\mu$l saline solution containing 6 g/kg body weight of each bioactive substance. Injection was done every 12 hours for five days. Forty-seven mice were implanted with the tumour as described above and left for seven days. After measuring the tumour diameter, the animals were divided into four groups. Three groups of 12 mice each, received S.C. injections every 12 hours for five days of 100 $\mu$l saline solution containing either 20 $\mu$g/kg body weight, 30 $\mu$g/kg body weight or 40 $\mu$g/kg body weight of octreotide, galanin and serotonin. The last group (11 mice) served as controls and received only saline solution.

At the end of the exponents, the animals were weighed and then killed by decapitation. The animals were dissected and the abdomen and thorax were exposed. The animals were then inspected for possible occurrence of metastasis. The tumours were dissected out carefully and the diameters and weight were determined. Three tissue samples from each tumour were cut perpendicular to the surface, two from the periphery and one from the middle, from each tumour. The tissue samples were fixed overnight in 4% buffered paraformaldehyde, embedded in paraffin wax and cut at 5 $\mu$m.

Food Consumption, Faeces Weight and Faeces Water Content

During the first three days after tumour implantation and the first three days of treatment, the food consumed by each mouse was measured as was the faeces weight and its water content. The food consumed by each mouse was calculated as the difference between the weight of the food at the beginning of the observation period and at the end of it. The faeces were collected, weighed and dried at 100° C. in an oven for 3 h and weighed again. The water content was calculated from the following formula: 100×(1-faeces weight after drying/faeces weight before drying).

Morphological and Morphometric Studies

The slides were coded and the performer was not aware of the identity of the sections. The sections were stained with haematoxylin-eosin, in order to determine the relative volume density of necrotic tissue and the blood vessels in the tumours.

Apoptosis was detected by in situ hybridisation using a kit (TA5411) from R&D Systems Inc (Minneapolis, Minn., USA). The kit detects DNA fragmentation. The fragments of DNA were detected by incorporating biotinylated nucleotides to the 3'OH ends of the DNA fragments, using terminal deoxynucleotidyl transferase (TdT). A streptavidin-conjugated horseradish peroxidase specifically binds to the biotinylated DNA fragments. The peroxidase was detected by diaminobenzidine tetrahydrochloride (DAB). The sections were counter-stained with methyl green. The in situ hybridisation was performed according to the protocols supplied by the manufacturers. Controls included nuclease-generated positive controls, unlabelled sample controls and labelled untreated sections from normal tissue (mouse colon).

To detect proliferation, the sections from the tumour tissue samples from all the animals were immunostained with the avidin-biotin-complex (ABC) method (Dakopatts, Glostrup, Denmark) as described earlier in detail (7). Briefly, the sections were immersed in 0.5% $H_2O_2$ in Tris-buffer, pH 7.6, for 10 min to inhibit the endogenous peroxidase. They were then incubated with 1% bovine serum albumin for 10 min to block the non-specific binding sites. The sections were incubated with proliferating cell nuclear antigen (PCNA) monocloxl antibody (code number M0879, Dakopatts) diluted 1:50 for 20 h at room temperature. Incubation with the secondary antibody, biotinylated swine anti-mouse IgG, diluted 1:200, was carried out at room temperature for 30 min. The sections were then incubated for another 30 min with the avidin-biotin-peroxidase complex, diluted 1:200, at room temperature. Peroxidase was detected by immersing the sections in 50 ml Tris-buffer containing 25 mg DAB and 10 $\mu$l of 30% $H_{22}$, followed by slight counterstaining in Mayer's haematoxylin. Specificity controls included negative controls and positive controls. As negative control, the sections were incubated with non-immune serum instead of the primary antibodies. Positive controls included immunostaining of sections from human colon adenocarcinoma.

Quantification was performed with the classical stereological point-counting method (8,9) as adapted for computerised image analysis (10). The Quantimet 500 MC image processing and analysis system (Leica, Cambridge, UK) linked to an Olympus microscope, type BXSO was used. The software used were "QWIN", a windows-based image analysis program from Leica and QUIPS, and an interactive program. Quantification was performed using X10 and X40 objectives. At these magnifications each pixel of the image corresponded to 0.83 and 0.21 $\mu$m, respectively and each field in the monitor represented a tissue area of 0.17 and 0.009 mm$^2$, respectively. Briefly, an automated standard sequence analysis operation was applied, in which a regular 400-point lattice was superimposed on the frame containing the tissue. Points covering tissue other than the tumour were erased and the points covering the object to be measured were pointed out with the computer "mouse", by clicking on the mouse, a series of blue highlight points appeared. The ratio of points lying on the object to be measured vs. those lying on the tumour in each field was tabulated. The sum of all fields in the specimen was computed and statistically analysed automatically.

To determine the relative volume density of necrotic tissue and of tumour blood vessels, a total of 30 fields, 10 fields from each of the tree tissue samples, from each tumour spread randomly were measured. An objective X10 was used. Apoptotic and proliferating nuclei volume density were measured in 45 randomly chosen fields, 15 from each of the three tissue samples from each tumour. An X40 objective was used.

Statistical Analysis

Companion between groups was performed with the one-way analysis of variance (ANOVA) and Tukey-Kramer multiple comparisons as post-test, when Bartlett's test for homogeneity of variance showed that the difference between SDs was not significant. When Bartlett's test was significant, Kruskal-Wallis non-parametric ANOVA test was used with Dunn's multiple comparisons as post-test. P values below 0.05 were considered significant.

(a) Results

The treated animals felt well during the experiments and did not differ from controls. One mouse died in the group treated with 20 μg/kg body weight octreotide, galianin and serotonin. Dissection of this animal revealed metastasis in the liver and regional mesentric lymph nodes. Another mouse died in the group injected with 30 μg/kg body weight bioactive substances. Dissection showed metastasis in the regional mesentric lymph nodes. Still another mouse died in the group that received 40 μg/kg body weight bioactive substances. Dissection did not show any metastasis or macroscopic abnormalities. At the end of the experiments, dissection of the mice showed that one had metastasis in the liver and regional mesenteric lymph nodes in the group that had received 40 μg/kg body weight octreotide, galanin and serotonin. The other mice did not show any sign of metastasis.

Tumour Volume and Weight

There was no statistical difference in the tumour volume in animal groups that received low doses (3 and 6 μg/kg body weight) of bioactive substances and controls (P=0.7). On the other hand, there was a statistical difference between animal groups treated with high doses (20, 30 and 40 μg/kg body weight) of bioactive substances (P=0.003). The groups that received 20, 30 and 40 μg were significantly different from controls regarding the tumour volume (P<0.05, <0.05 and <0.01, respectively). There was no difference between the group treated with 20 μg/kg body weight bioactive substances vs. groups treated with 30 or 40, nor there was any difference between the group treated with 30 μg/kg body weight bioactive substances vs. that received 40 (FIG. 8). There was no statistically significant difference in the mice treated with low or high doses of bioactive substances regarding tumour weight (P=0.6 and 0.7, respectively) (FIG. 9).

Food Consumption, Body Weight Faeces Weight and Faeces Water Content

The results of measurements of food consumption, faeces weight and faeces water content before and after treatment are summarised in Tables 1 and 2. There was no statistically significant difference between animal groups before treatment with either low or high doses of bioactive substances and controls regarding faeces weight, faeces water content, animal weight or food consumption. Neither was there any difference between these groups after treatment.

Morphological and Morphometeric Studies

There was no statistically significant difference between animal groups treated with low doses of bioactive substances and controls regarding the volume density of tumour necrotic tissue (P=0.2). The volume density of necrotic tissue in the tumours of groups treated with high doses of bioactive substances and controls was significantly different (P=0.002). The animals treated with 20, 30 and 40 μg/kg body weight of bioactive substances showed significantly higher volume density of necrotic tissue in the tumours than that of controls (P<0.01, <0.01 and <0.01, respectively). There was no difference between groups treated with different doses (FIG. 10).

The relative volume density of blood vessels in the tumours in groups treated with both low and high doses of bio active substances and controls was significantly different (P=0.0005 and <0.0001). Relative volume density of blood vessels in the mice treated with 3, 6, 20, 30 and 40 μg/kg body weight bioactive substances was significantly lower than that of controls (P<0.01, <0.001, <0.001, <0.001, <0.001, respectively). There was no statistically significant difference between the treated groups (FIGS. 11 and 12).

There was no statistically significant difference between he groups treated with low doses of bioactive substances and controls regarding the relative volume density of apoptotic nuclei (P=0.2). There was, however, a statistically significant difference between animals treated with high doses of bioactive substances and controls (P<0.001). The relative volume density of apoptotic nuclei of the animal group treated with 20 μg was significantly higher than controls and those treated with 30 and 40 μg (P<0.001, <0.05 and <0.05, respectively). There was no statistically significant difference between mice that received 30 or 40 μg and controls (FIGS. 12 and 13). The volume density of proliferating nuclei in animals treated with both low and high doses of bioactive substances and controls showed no statistically significant difference (P=0.9 and 0.2, respectively) (FIG. 14).

Discussion

The present observations confirm our earlier findings (6) that triple therapy with octeotide, galanin and serotonin is a tumour regression treatment for a rat colon carcinoma This treatment induces tumour necrosis and increases apoptosis. Tumour necrosis seems to be caused by tumour ischemia. This may be a result of the reduction in tumour blood flow, which is caused by reduction in the number the constriction of tumour-feeding arterioles caused by serotonin (6,11). This therapy could, therefore be combined with chemotherapy drugs that reduce tumour growth such as fluropyrimidines, ralti trexed and platinum-based agents to enhance and increase the treatment effect.

In the present study, five days triple therapy with low doses (3 and 6 μg/kg body weight) of octreotide, galanin and serotoxiin did not significantly reduce the volume or weight of the tumour, nor did it increase necrosis or apoptosis of a rat colonic adenocarcinoma. This therapy on the other had, decreased the relative volume density of tumour-feeding blood vessels, an effect hat may be attributed to galanin (6). Treatment with high doses (20, 30 and 40 μg/kg body weight), however, reduced the tumour volume, the relative volume density of tumour-feeding blood vessels and increased the relative volume density of necrotic tumour tissue. In animals treated with 20 μg but not those treated with 30 or 40 μg/kg body weight of bioactive substances, the relative volume density of apoptotic nuclei increased. It is noteworthy that despite the reduced tumour volume in animal groups treated with high doses of bioactive substances, the tumour weight did not differ from that of controls. In a previous study where the same tumour was treated with 10 µg/kg body weight of the same bioactive substances, both the tumour volume and weight were reduced. The tumour weight in animal groups treated with high doses of bioactive substances consisted, however, of about 40% necrotic tissues. As it has been shown earlier (6), triple therapy with either low or high doses of octreotide, galanin and serotonin had no effect on tumour proliferation.

In a previous report (6), where triple therapy with octreotide, galanin and serotonin was applied, the morphometric method used for apoptosis and proliferation was labelling index, which is usually used in this connection (12). In the present study, another morphometric method was used, namely the classical stereological point-counting method. This method was chosen in order to verify whether or not similar results to our earlier studies (6) could be obtained regardless of the morphometric method applied. Furthermore, the point-counting method is less time consuming (10) and therefore allows quantification of more fields of the tumour tissue. There was no statistically significant difference between tumours treated with 20, 30 or 40 µg/kg body weight of octreotide, galanin and serotonin regarding the reduction of tumour volume and tumour-feeding blood vessels or increased necrosis. It is reasonable, therefore, to conclude that increasing the dose of the triple therapy over 2 µg/kg body weight dose not intensify the effects of these bioactive substances on the tumour.

Despite the relatively high doses of octreotide, galanin and serotonin used in treating the mice bearing a rat colon carcinoma, no apparent side-effects were observed during the time of treatment. Thus, the mice treated with both low and high doses of these bioactive substances seemed to be well and did not differ from controls. No emesis, or declined body weight, or worsened appetite were found. Neither were there any signs of diarrhea or constipation. It seems that the combination of these three bioactive substances eliminates the side-effects of each other. Thus, whereas serotonin stimulates intestinal secretion and causes diarrhoea (13,14), somatostatin has an anti-secretory effect and is usually used as a drug against severe diarrhoea (5,16). Moreover, while serotonin stimulates gut motility (13,14), galanin and somatostatin inhibit gut motility (15–17). The present treatment regime seems therefore, to be, tolerable. This is important for its possible clinical use in the future.

The present study confirms an earlier report (6) that triple therapy with octreotide, galanin and serotonin causes regression of a rat colon carcinoma. It further showed that optimum treatment dose is 10–20 µg/kg body weight of each bioactive substance. Doses below 10 µg do not have a maximal effect and doses over 20 µ☐g do not intensify the effect of treatment. Moreover, this therapy regime does not show apparent side-effects in the experiments done on mice. Though these results are promising and may offer a possible treatment for regression of colon cancer, one must keep in mind that more tumours should be examined, especially human colon carcinoma, as colon carcinoma shows heterogeneity in its response to different therapies. Whether or not the present findings will be of any use in the treatment of patients with colorectal cancer is still far from known.

It should be understood that modifications can be made to the embodiments disclosed herein. Therefore the above description should not be construed as limiting, but merely as exemplification of preferred embodiments. Those skilled in the art will envision other modifications within the scope of the claims appended hereto.

REFERENCES

All of which Appearing Below are Incorporated by Reference into the Present Description Alonos M, Galera M J, Reyes G, Calabuig A, Vinals A, Rius X(1992) Effects of pentagastrin and somatostatin analog (SMS 201-995) on growth of CT26 in vivo adenocarcinoma of the colon. Surg Gynecol Obestet 175:441–444.

Baguley B C, Zhuang L, Kestell P (1997) Increased plasma serotonin following treatment with flavone-8-acetic acid, 5,6-dmethylxanthrenone4acetic acid, vinblastine and colchicine. Relation to vascular effect. Oncol Res 9:55–60.

Baguley B C, Cole G. Thomsen L L, Li Z (1993) Serotonin involvement in the antitumour and host effects of flavone-8-acetic acid and and 5,6-dimethylxanthrenone-4acetic acid. Cancer Chemother Pharmacol 33:77–81.

Barkla D H, Tutton P J M (1981) Influence of histamine and serotonin antagonists on the growth of xenografted human colorectal tumours. J Natl Cancer Inst 67:1207–1211.

Berger T, Eklund G. Mellner C, Phil B. Wenckert A (1973) Carcinoma of the colon and rectum in a defined population. An epidemiological, clinical and post-mortem investigation of colorectal carcinoma and coexisting benign polyps in Malmö, Sweden. Acta Chir Scand Suppl 438:1–86.

El-Salhy M, Stenling R, Grimelius L (1993) Peptidergic innervation and endocrine cells in the human liver. Scand J Gastroenterol 128:809–815.

El-Salhy M, Norrgård O, Boström A (1998a) Low levels of colonic somatostatin and galanin in patients with colon carcinoma. GI Cancer 2:221–225.

El-Salhy M, Mahdavi J, Norrgård Ö (1998b)Colonic endocrine cells in patients with carcinoma of the colon. Euro J Gastroenterol Hepatol 10:517–522.

El-Salhy M, Norrgård Ö Franzén L, Forsgren S (1998c) Colonic endocrine cells in patients with carcinoma of the rectum with special regard to preoperative irradiation. GI Cancer 2:285–292.

Gamet L, Mutrat J C, Remaury A, Remesy C, Valet P, Paris H, and Denis-Pouxviel C (1992) Vasoactive intestinal peptide and forskolin regulate proliferation of HT29 human colon adenocarcinoma cell line. J Cell Physiol 150:501–509.

Goldberg R M, Moertel C G, Wieand H S, Krool J E, Schut A J, Veeder M H, Mailliard J A, Dalton R J (1995) A phase III evaluation of somatostatin analogue (octreotise) in the treatment of patients with asymptomatic advanced colon carcinoma. Cancer 76:961–966.

Hill D J (1991) Neuropeptides and cell proliferation. In Neuropeptides function in gastrointestinal tract.Daniel E E. (ed) pp 479–490. CRC Press: Boca Raton.

Huhnt W, Lubbe A S (1995) Growth, microvessel density and tumour cell invasion of human colon adenocarcinoma under repeated treatment with hyperthermia and serotonin. J Cancer Res Clin Oncol121:423–428.

Laemel E, Stücker O, Darmon P-L, Vicaut E (1998) Characterization of the specific response to serotonin of mouse tumour-feeding arterioles. Int J Radiat Biol 74:379–386.

Iishi H, Tatsuta M, Baba M, Uehara H. Yano H, Nakaizumi A (1995) Chemoprevention by galanin against colon carcinogenesis induced by azoxymethane in wistar rats. Int J Cancer 61:861–863.

Midgely O R, Kerr D (1999) Colorectal cancer. The Lancet 353:391–399.

Muhiuddin M, Karks G (1991). Adjuvant radiation therapy for colon and rectum cancer. Oncol 18:11–420.

Narayan S, Guo Y S, Townsend C M Jr, Singh P (1990) Specific binding and growth effects of bombesin-related peptides on mouse colon cancer cells in vitro. Cancer Res 50:6772–6778.

O'Dorisio M (1987) Neuropeptides and gastrointestinal immunity. Am J Med 81(Suppl 6B):74–82.

Palmqvist R, Öberg Å, Bergström C, Rutegård J N, Zackrisson B, Stenling R (1998) Systematic heterogeneity and prognostic significance of cell proliferation in colorectal cancer. Br J cancer 77:917–925.

Qin Y, Schally A V, Willems G (1992) Treatment of liver metatases of human colon cancer in nude mice with somatostatin analogue RC-160. Int J Cancer 52:791–796.

Radulovic S, Schally A V, Reile H, Halmos G, Szepeshazi K, Groot K, Milovanovic S, Miller G, Tang T (1994) Inhibitory effects of antagonists of bombesin/gastrin releasing peptide (GRP) and somatostatin analog (RC-160) on growth of TH-29 human colon cancers in nude mice. Acta Oncol 33:693–701.

Robbins R J (1996) Somatostin and cancer. Metab Clin Exp 45:98–100.

Smith J P, Solomon T E (1988) Effects of gastrin, proglumide, and somatostatin on growth of human colon cancer. Gastroenterology 95:1541–1548.

Smith J P, Doll D, Croitoru R, Thornton C, Peryy M C (1994) Octreotide has no effect on advanced colon cancer. J Clin Gastroenterol 18:245–247.

Tuttox P J M, Barkla D H (1978) The influence of serotonin on the mitotic rate in the colonic crypt epithelium and in colonic adenocarcinoma in rats. Clin Exp Pharmacol Physiol 5:91–94.

Valone F H, Kohler M, Fisher K, Hannigan J, Flam M, Gandara D, Hendrickson C, Richman E, Yu K P (1987) A northern California oncology group randomized trial of Leucovorin plus 5-fluorouracil versus sequential methotrexate, 5-fluorouacil and leucovorin in patients with advanced colorectal cancer who failed treatment with 5-fluorouracil or 5-fluorodeoxyuridine alone. NCI Monographs 5:175–177.

van-Tol E A, Verspaget H W, Pena A S, Jansen J B, Aparicio-Pages M N, Lambers C B (1991) Modulatory effects of VIP and related peptides from the gastrointestinal tract on cell mediated cytotoxicity against tumour cells in vitro. Immunol Invest 20:257–267.

Weibel E, Elias H (1967) Introduction to stereologic principles. In Quantitative methods in morphology Weibel E, Elias H (eds)pp 89–98. Springer-Verlag: Berlin.

Weibel E. Stäubli R H, Hess F A (1969) Correlated morphometric and biochemical studies on the liver cell. I. Morphometric model, stereologic methods, and normal morphometric data for rat liver. J Cell Biol 42:68–91.

Winsett O E, Townsend C M Jr, Glass C J, Thompson J C (1986) Gastrin stimulates growth of colon cancer, Surgery 99:302–307.

Yoshinaga K Evers B M, Izukura M, Parekh D, Townsend C M Jr, Thompson J C (1992) Neurotensin stimulates growth of colon cancer, Surg Oncol 1:127–134.

REFERENCES

Example 2

1. Hill D J. Neuropeptides and cell proliferation. In: Daniel E E, ed. Neuropeptides function in gastrointestinal tract. Boca Raton, CRC Press. 1991, 479–490.
2. O'Dorisio M. Neuropeptides and gastrointestinal immunity. Am J Med 1987, 81(Suppl 6B), 74–82.
3. El-Salhy M, Norrgåd O, Boström A. Low levels of colonic somatostatin and galanin in patients with colon carcinoma. GI Cancer 1998, 2, 221–225.
4. El-Salhy, M, Mahdavi, J, Norgård, Ö. Colonic endocrine cells in patients with carcinoma of the colon. Euro J Gastroenterol Hepatol 1998, 10, 517–522.
5. El-Salhy M., Norrgård Ö, Franzén L, Forsgren S. Colonic endocrine cells in patients with carcinoma of the rectum with special regard to preoperative irradiation. GI Cancer 1998, 2, 285–292.
6. El-Salhy M, Sitohy B, Norrgård Ö. Triple therapy with octreotide, galanin and serotonin reduces the size and blood vessel density and increases apoptosis in a rat colon carcinoma. Submitted 2001.
7. El-Salhy M, Stenling R, Grimelius L. Peptidergic innervation and endocrine cells in the human liver. Scand J Gastroenterol 1993, 28, 809–815.
8. Weibel E, Elias H. Introduction to stereologic principles. In. Weibel E, Elias H, eds. Quantitative methods in morphology. Berlin, Springer-Verlag, 1967, 89–98.
9. Weibel E, Stäubli R H, Hess F A. Correlated morphometric and biochemical studies on the liver cell. I. Morphoinetric model, stereologic methods, and normal morphometric data for rat liver. J Cell Biol, 1969, 42, 68–91.
10. El-Salhy M, Sandström O, Näsström E, Mustajbasic M, Zachrisson S. Application of computer image analysis in endocrine cell quantification. Histochem J 1977, 29, 249–256.
11. Laemel E, Stücker O, Darmon P-L, Vicaut E. Characterization of the specific response to serotonin of mouse tumour-feeding arterioles. Int J Radiat Biol 1998, 74, 379–386.
12. Palmqvist R, Öberg Å, Bergström C, Rutegård J N, Zackrisson B, Stenling R. Systematic heterogeneity and prognostic significance of cell proliferation in colorectal cancer. Br J cancer 1998, 77, 917–925.
13. Goyal P K, Hirano I. Mechanisms of disease: The enteric nervous system. N Engl J Med 1996, 344, 1106–1115.
14. Burks T. Neurotransmission and neurotansmitters. In: Johansson L, Alpers D, Christensen J, Walsh J, eds. Physiology of the gastrointestinal tract.$3^{rd}$ edition. New York, Raven Press, 1994, 211–242.
15. Walsh J. Gastrointesial hormones. In Johansson L, Alpers D, Christensen J, Walsh J, eds. Physiology of the gastrointestinal tract.$3^{rd}$ edition. New York, Raven Press, 1994, 1–128.
16. Chiba T, Yamada T. Gut somatostatin. In walsh J, Dockray G J, eds.Gut peptides: Biochemistry and physiology. New York, RavenPress, 1994, 125–145.
17. Rökaeus Å. Galanin. In walsh J, Dockay G J, eds.Gut peptides: Biochemistry and physiology. New York, Raven Press, 1994, 123–145.

TABLE 1

Faeces weight, faeces water content, animal weight and food consumption of controls and mice before and after treatment with low doses of octrectide, galanin and serotonin (mean ± SE)

| | Faeces Weight (g)* | | Water content (%)* | | Animal weight (g) | | Food consumption (g)* | |
|---|---|---|---|---|---|---|---|---|
| | Before | After | Before | After | Before | After | Before | After |
| Controls | 4.4 ± 0.1 | 5.2 ± 0.2 | 11.8 ± 0.8 | 12.9 ± 0.8 | 21.7 ± 0.4 | 20.2 ± 0.4 | 33.35 ± 1.1 | 23.1 ± 0.7 |
| 3 µg/kg | 4 ± 0.2 | 4.6 ± 0.2 | 13.2 ± 1.1 | 18.2 ± 2.6 | 20.9 ± 0.5 | 19.8 ± 0.5 | 19.5 ± 0.9 | 20.1 ± 0.6 |
| 6 µg/kg | 4.3 ± 0.2 | 5 ± 0.3 | 12.3 ± 0.9 | 14.8 ± 1 | 20.8 ± 0.6 | 17.5 ± 0.43 | 21.1 ± 0.6 | 21.5 ± 1 |

*per 3 days

TABLE 2

Faeces weight, faeces water content, animal weight and food consumption of controls and mice before and after treatment with low doses of octreotide, galanin and serotonin (mean ± SE)

| | Faeces Weight (g)* | | Water content (%)* | | Animal weight (g) | | Food consumption (g)* | |
|---|---|---|---|---|---|---|---|---|
| | Before | After | Before | After | Before | After | Before | After |
| Controls | 3.3 ± 0.1 | 3.3 ± 0.2 | 12.9 ± 0.7 | 8.6 ± 0.6 | 16.8 ± 0.4 | 18.3 ± 0.4 | 20.5 ± 0.8 | 18.7 ± 0.7 |
| 20 µg/kg | 3.5 ± 0.2 | 3.1 ± 0.3 | 10.7 ± 1.5 | 6.3 ± 0.6 | 18.4 ± 0.5 | 18 ± 0.4 | 21 ± 0.7 | 17.2 ± 1.2 |
| 30 µg/kg | 3.6 ± 0.12 | 3.4 ± 0.2 | 11.9 ± 0.9 | 8.6 ± 0.5 | 18.6 ± 0.4 | 17.5 ± 0.4 | 21.7 ± 0.4 | 16.8 ± 1.6 |
| 40 µg/kg | 3.3 ± 0.1 | 3.6 ± 0.2 | 10.5 ± 0.8 | 7.2 ± 0.5 | 18.9 ± 0.3 | 18.2 ± 0.2 | 21.7 ± 0.8 | 19.5 ± 1 |

*per 3 days

What is claimed is:

1. A pharmaceutical composition effective for treating human or non-human neoplastic disorder, comprising pharmaceutically effective amounts of each of galanin, octreotide and serotonin, in admixture with a pharmaceutically acceptable carrier.

2. A pharmaceutical composition according to claim 1, wherein said disorder is a colorectal disorder.

3. A method for treatment of neoplastic disorders in a human or non-human animal, comprising administering to such an animal in need of the same, a pharmaceutically effective amount of a pharmaceutical composition as claimed in claim 1.

4. A method as claimed in claim 3, wherein said effective amount is about 10 µg/kg body weight to about 60 µg/kg body weight of each of galanin, octreotide and serotonin.

5. A method according to claim 3, wherein said effective amount is about 10 µg/kg to about 20 µg/kg of each of galanin, octreotide and serotonin.

6. A method according to claim 3, wherein said disorder is a colorectal disorder.

* * * * *